(12) United States Patent
Mazlish

(10) Patent No.: US 9,833,191 B2
(45) Date of Patent: Dec. 5, 2017

(54) COMPUTER-BASED DIABETES MANAGEMENT

(71) Applicant: BIGFOOT BIOMEDICAL, INC., Milpitas, CA (US)

(72) Inventor: Bryan Mazlish, New York, NY (US)

(73) Assignee: BIGFOOT BIOMEDICAL, INC., Milpitas, CA (US)

(*) Notice: Subject to any disclaimer, the term of this patent is extended or adjusted under 35 U.S.C. 154(b) by 681 days.

(21) Appl. No.: 13/738,466

(22) Filed: Jan. 10, 2013

(65) Prior Publication Data

US 2014/0128705 A1  May 8, 2014

Related U.S. Application Data

(60) Provisional application No. 61/723,577, filed on Nov. 7, 2012.

(51) Int. Cl.
*A61B 5/00* (2006.01)
*A61B 5/145* (2006.01)

(52) U.S. Cl.
CPC ........ *A61B 5/4866* (2013.01); *A61B 5/14532* (2013.01); *A61B 5/4833* (2013.01); *A61B 5/4839* (2013.01); *A61B 5/4848* (2013.01); *A61B 5/7225* (2013.01);
(Continued)

(58) Field of Classification Search
None
See application file for complete search history.

(56) References Cited

U.S. PATENT DOCUMENTS

| 4,464,170 A | 8/1984 | Clemens et al. |
| 5,822,715 A | 10/1998 | Worthington et al. |
| 5,971,922 A | 10/1999 | Arita et al. |

(Continued)

FOREIGN PATENT DOCUMENTS

| JP | 2008545454 A | 12/2008 |
| JP | 2010531678 A | 9/2010 |

(Continued)

OTHER PUBLICATIONS

International Search Report and Written Opinion for PCT/US2013/068399 dated Dec. 12, 2013.
(Continued)

*Primary Examiner* — Jacqueline Cheng
*Assistant Examiner* — Jairo Portillo
(74) *Attorney, Agent, or Firm* — Maschoff Brennan

(57) ABSTRACT

A computer-based method includes receiving, from a computer-based user interface, user-specified information about one or more events influential on the user's blood glucose level, generating, with a computer-based processor, a plurality of estimated trajectories of the user's blood glucose level as influenced by the one or more events, receiving a set of data that represents actual blood glucose measurements for the user, and identifying, with the computer-based processor, which of the estimated trajectories represents a best fit to the set of data that represents the actual blood glucose measurements for the user. At least some of the actual blood glucose measurements occurred later in time than a start time of the one or more events influential on the user's blood glucose level. A computer-based system is provided for implementing the method.

43 Claims, 14 Drawing Sheets

(52) U.S. Cl.
CPC .......... *A61B 5/7246* (2013.01); *A61B 5/7275* (2013.01); *A61B 5/743* (2013.01); *A61B 5/7475* (2013.01)

(56) References Cited

U.S. PATENT DOCUMENTS

| | | | |
|---|---|---|---|
| 6,081,786 | A | 6/2000 | Barry et al. |
| 6,379,301 | B1 | 4/2002 | Worthington et al. |
| 6,544,212 | B2 | 4/2003 | Galley et al. |
| 6,595,919 | B2 | 7/2003 | Berner et al. |
| 6,691,043 | B2 | 2/2004 | Ribeiro, Jr. |
| 6,835,175 | B1 | 12/2004 | Porumbescu |
| 6,925,393 | B1* | 8/2005 | Kalatz ................. G06F 19/3406 702/19 |
| 7,025,743 | B2 | 4/2006 | Mann et al. |
| 7,137,951 | B2 | 11/2006 | Pilarski |
| 7,266,400 | B2 | 9/2007 | Fine et al. |
| 7,570,980 | B2 | 8/2009 | Ginsberg |
| 7,651,845 | B2 | 1/2010 | Doyle, III et al. |
| 7,766,829 | B2 | 8/2010 | Sloan et al. |
| 7,806,854 | B2 | 10/2010 | Damiano et al. |
| 7,850,641 | B2 | 12/2010 | Lebel et al. |
| 7,920,998 | B2 | 4/2011 | Brown |
| 7,949,507 | B2 | 5/2011 | Brown |
| 7,979,259 | B2 | 7/2011 | Brown |
| RE43,316 | E | 4/2012 | Brown et al. |
| 8,147,446 | B2 | 4/2012 | Yodfat et al. |
| 8,204,729 | B2 | 6/2012 | Sher |
| 8,206,296 | B2 | 6/2012 | Jennewine |
| 8,257,300 | B2 | 9/2012 | Budiman et al. |
| 8,265,726 | B2 | 9/2012 | Say et al. |
| 8,273,022 | B2 | 9/2012 | Say et al. |
| 8,298,184 | B2 | 10/2012 | Diperna et al. |
| 2003/0163223 | A1 | 8/2003 | Blomquist |
| 2004/0220517 | A1 | 11/2004 | Starkweather et al. |
| 2005/0038680 | A1* | 2/2005 | McMahon ........................ 705/3 |
| 2005/0272640 | A1* | 12/2005 | Doyle et al. ........................ 514/3 |
| 2006/0253067 | A1 | 11/2006 | Staib et al. |
| 2007/0060869 | A1 | 3/2007 | Tolle et al. |
| 2007/0100222 | A1 | 5/2007 | Mastrototaro et al. |
| 2008/0201325 | A1 | 8/2008 | Doniger et al. |
| 2008/0208113 | A1 | 8/2008 | Damiano et al. |
| 2008/0228056 | A1 | 9/2008 | Blomquist et al. |
| 2008/0234663 | A1 | 9/2008 | Yodfat et al. |
| 2008/0250341 | A1* | 10/2008 | Dlugos et al. ................. 715/771 |
| 2008/0269714 | A1 | 10/2008 | Mastrototaro et al. |
| 2008/0306353 | A1 | 12/2008 | Douglas et al. |
| 2008/0319384 | A1 | 12/2008 | Yodfat et al. |
| 2009/0112154 | A1 | 4/2009 | Montgomery et al. |
| 2009/0164251 | A1 | 6/2009 | Hayter |
| 2010/0049022 | A1* | 2/2010 | Parris ................. A61B 5/14532 600/347 |
| 2010/0057042 | A1 | 3/2010 | Hayter |
| 2010/0075353 | A1* | 3/2010 | Heaton ........................ 435/14 |
| 2010/0082167 | A1 | 4/2010 | Haueter et al. |
| 2010/0121170 | A1 | 5/2010 | Rule |
| 2010/0137788 | A1 | 6/2010 | Braithwaite et al. |
| 2010/0145262 | A1 | 6/2010 | Bengtsson et al. |
| 2010/0174266 | A1 | 7/2010 | Estes |
| 2010/0256466 | A1 | 10/2010 | Shekalim et al. |
| 2010/0262117 | A1 | 10/2010 | Magni et al. |
| 2010/0292634 | A1* | 11/2010 | Kircher, Jr. ........ A61B 5/14532 604/66 |
| 2010/0295686 | A1 | 11/2010 | Sloan et al. |
| 2010/0317952 | A1 | 12/2010 | Budiman et al. |
| 2011/0009725 | A1 | 1/2011 | Hill et al. |
| 2011/0009813 | A1 | 1/2011 | Rankers |
| 2011/0021898 | A1 | 1/2011 | Wei et al. |
| 2011/0098548 | A1 | 4/2011 | Budiman et al. |
| 2011/0098674 | A1 | 4/2011 | Vicente et al. |
| 2011/0106011 | A1 | 5/2011 | Cinar et al. |
| 2011/0106050 | A1 | 5/2011 | Yodfat et al. |
| 2011/0160555 | A1 | 6/2011 | Reifman et al. |
| 2011/0266999 | A1 | 11/2011 | Yodfat et al. |
| 2012/0010592 | A1 | 1/2012 | Brown |
| 2012/0059351 | A1 | 3/2012 | Nordh |
| 2012/0136336 | A1 | 5/2012 | Mastrototaro et al. |
| 2012/0165638 | A1 | 6/2012 | Duke et al. |
| 2012/0246106 | A1 | 9/2012 | Atlas et al. |
| 2012/0277667 | A1 | 11/2012 | Yodfat et al. |
| 2012/0283694 | A1 | 11/2012 | Yodfat et al. |
| 2013/0030358 | A1 | 1/2013 | Yodfat et al. |
| 2013/0046281 | A1 | 2/2013 | Javitt |
| 2013/0072872 | A1 | 3/2013 | Yodfat et al. |
| 2013/0079613 | A1 | 3/2013 | Kovatchev et al. |
| 2013/0245547 | A1 | 9/2013 | El-Khatib et al. |
| 2014/0066887 | A1 | 3/2014 | Mastrototaro et al. |
| 2014/0309615 | A1 | 10/2014 | Mazlish |
| 2014/0350369 | A1 | 11/2014 | Budiman et al. |
| 2015/0289823 | A1 | 10/2015 | Rack-Gomer et al. |

FOREIGN PATENT DOCUMENTS

| | | |
|---|---|---|
| WO | 2006124716 A3 | 11/2006 |
| WO | 2008057384 A3 | 5/2008 |
| WO | 2008157780 A1 | 12/2008 |
| WO | WO2013/096769 A1 | 6/2013 |

OTHER PUBLICATIONS

Karena L. Swan M.D., et al, "Effect of Age of Infusion Site and Type of Rapid-Acting Analog on Pharmacodynamic Parameters of Insulin Boluses in Youth with Type 1 Diabetes Receiving Insulin Pump Therapy"; Diabetes Care, Feb. 2009, vol. 32 No. 2, pp. 240-244.

Mark E. Pennant Ph.D. et al, "Insulin Administration and Rate of Glucose Appearance in People with Type 1 Diabetes"; Diabetes Care, Nov. 2008, vol. 31, No. 11, pp. 2183-2187.

Mudaliar et al.; Insulin aspart (B28 Asp-insulin): A fast-acting analog of human insulin; Diabetes Care; 22(9); pp. 1501-1506; Sep. 1999.

Mazlish; U.S. Appl. No. 14/733,567 entitled "Insulin delivery systems and methods," filed Jun. 8, 2015.

Search Report received in International Application No. PCT/US17/34012, dated Aug. 17, 2017.

Written Opinion of the International Searching Authority, as issued in connection with the International Patent Application No. PCT/US17/34012 dated Aug. 17, 2017.

* cited by examiner

User-Specific, Diabetes-Related Therapy Parameters

| | Low | High |
|---|---|---|
| insulin-to-carbohydrate ratio | | |
| insulin sensitivity factor | | |
| duration of insulin action | | |
| time for carbohydrate absorption | | |
| duration of exercise effect | | |
| exercise per hour to carb | | |

FIG. 4

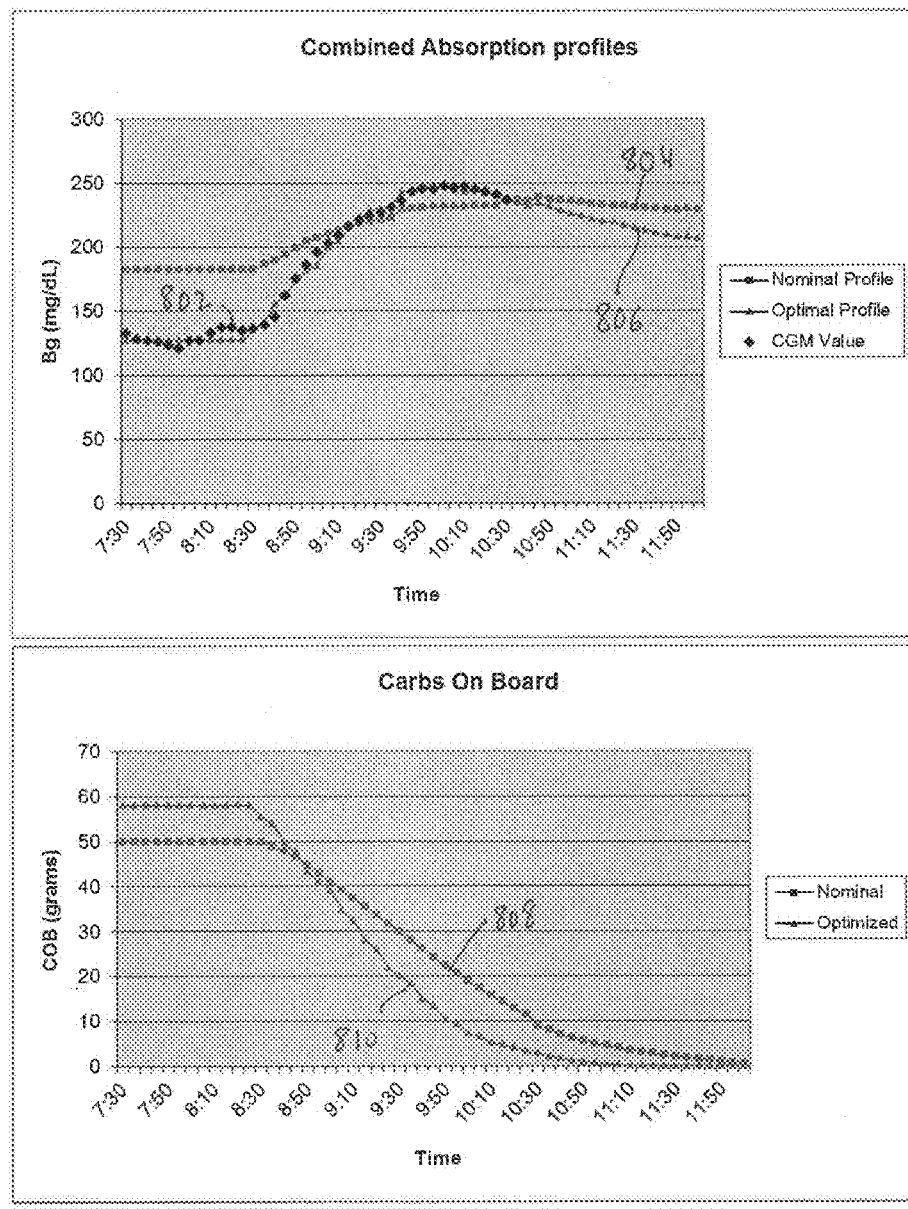

COMPUTER-BASED DIABETES MANAGEMENT

CROSS-REFERENCE TO RELATED APPLICATION

This application claims the benefit of U.S. Provisional Application No. 61/723,577, filed Nov. 7, 2012, entitled COMPUTER-BASED DIABETES MANAGEMENT.

FIELD OF THE INVENTION

The present application relates to computer-based diabetes management.

BACKGROUND

Diabetes is a group of metabolic diseases which manifests in a person as a high blood glucose level, either because the person's pancreas does not produce enough insulin, or because the person's cells do not respond sufficiently to the insulin that is produced. The lack of insulin or insulin sensitivity prevents glucose from entering the person's cells and thus creates an excess of glucose in the blood stream. Intensive insulin therapy is used to mitigate the elevated glucose levels by allowing the glucose to enter the cells. People with diabetes manage the disease by trying to keeping blood glucose levels within the normal range by adjusting their diet, exercise, medications and insulin dosing.

While intensive insulin therapy can mitigate elevated glucose levels, it can also cause conditions of hypoglycemia that range from mildly unsafe to severe and dangerous. A patient must balance the dosing of insulin to mitigate hyperglycemia while not overdosing and causing hypoglycemia. This precarious balance creates a constant optimization problem for patients with diabetes. The present disclosure is directed to assisting patients in the visualization and determination of how to balance their insulin needs.

SUMMARY OF THE INVENTION

In one aspect, a computer-based method includes receiving, from a computer-based user interface, user-specified information about one or more events influential on the user's blood glucose level. The method includes generating, with a computer-based processor, a plurality of estimated trajectories of the user's blood glucose level as influenced by the one or more events. The method also includes receiving a set of data that represents actual blood glucose measurements for the user (e.g., from a continuous glucose monitor). Then, the method includes identifying, with the computer-based processor, which of the estimated trajectories represents a best fit to the set of data that represents the actual blood glucose measurements for the user. Typically, at least some of the actual blood glucose measurements occurred later in time than a start time of the one or more events influential on the user's blood glucose level.

According to other aspects, computer systems to implement and computer-readable media with instructions to implement the techniques disclosed herein are disclosed.

In some implementations, one or more of the following advantages may be present.

For example, the user receives highly accurate estimated projection of the user's future blood glucose levels.

In addition, in certain implementations, the user may be given an, intuitive indication as to the accuracy the projection of future blood glucose levels.

Moreover, the methods and systems can include robust bolus and therapy calculation facilities.

Additionally, the methods and systems disclosed can include an insulin pump occlusion alarm that may detect that insulin delivery has ceased from the data input, rather than the currently used physical sensors on the insulin pump.

The methods and systems may also include novel alarm types that focus solely on actionable therapies rather than absolute glucose levels, thereby reducing nuisance alarming and general alarm fatigue.

Other features and advantages will be apparent from the description and drawings, and from the claims.

BRIEF DESCRIPTION OF THE DRAWINGS

FIG. 4 is a screenshot that may appear on the personal computing device in FIG. 1.

FIG. 8A includes a graph that represents actual blood glucose values, a nominal profile of estimated future blood glucose levels and an optimal profile of estimated blood glucose levels over time.

FIG. 8B includes a graph that represents a nominal profile of carbs-on-board and an optimized profile of carbs-on-board over time.

DETAILED DESCRIPTION

Figure 1:
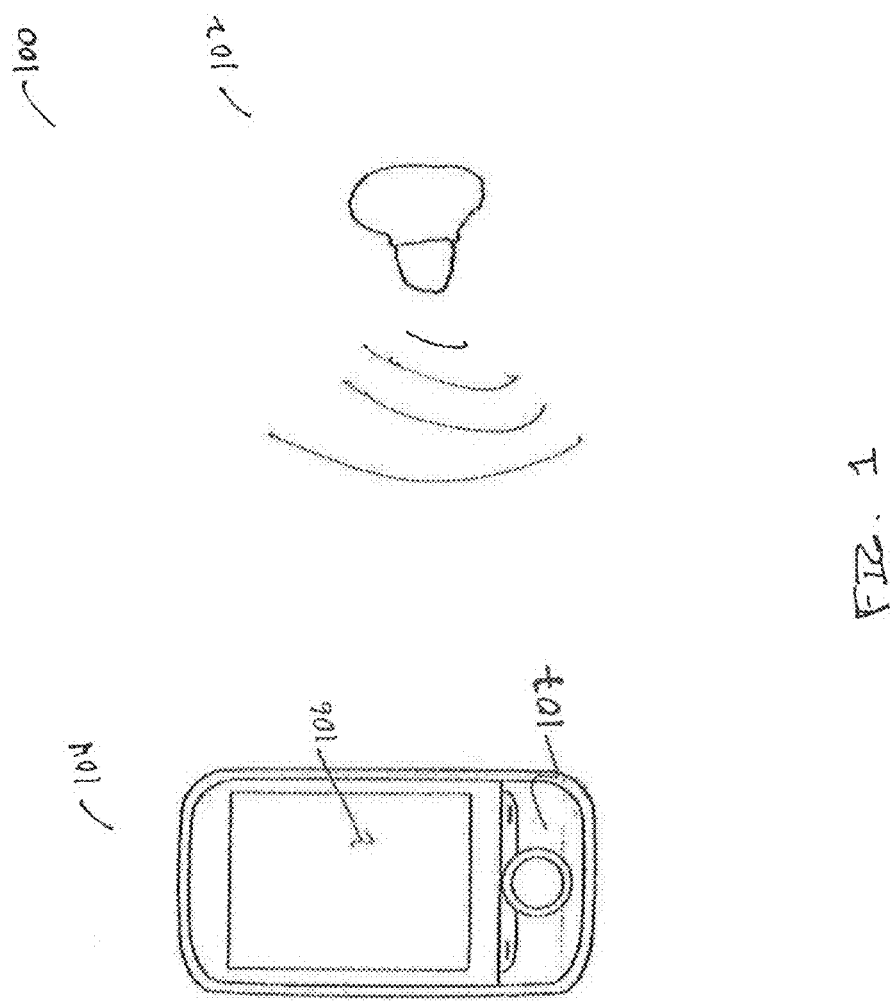
FIG. 1 is a schematic diagram showing one example of a computer system configured to implement one or more of the techniques disclosed herein.

FIG. 1 is a schematic representation of an exemplary system 100 configured to implement one or more of the techniques disclosed herein. The system 100 includes a glucose measurement device 102 and a personal computing device 104.

The glucose measurement device 102 can be any type of glucose measuring device including, for example, a continuous glucose monitor that determines a user's blood glucose levels on a continuous basis, typically every few minutes. Continuous glucose monitors generally include a disposable glucose sensor that the user can place under his or her skin to access blood or interstitial fluid and a non-implantable transmitter linked to the disposable glucose sensor and adapted to communicate to a remote receiver (e.g., a transceiver in the personal computing device 102).

In a typical implementation, the continuous glucose monitors measure the user's blood glucose levels by assessing the user's blood or interstitial fluid.

The personal computing device 104 can be any type of personal computing device, such as a smartphone, tablet computer, or the like. In the illustrated implementation, the personal computing device 104 is a handheld mobile device that includes an interactive touchscreen. The interactive touchscreen functions as a computer-based visual display that presents various data, information and interactive features to the user and as a computer-based user interface that enables the user to enter information into or interact with the interactive features via the touchscreen. For example, in some implementations, the user can enter information by touching a touch-responsive keyboard on the touchscreen 106.

The personal computing device may include other data input or interactive mechanisms 107, as well. These may include, for example, track balls, contact pads, hardware-based keyboards, etc.

In some implementations, the personal computing device 104 also has built-in speakers, vibrators or the like (not shown in FIG. 1) that are configured to produce sounds, tactile outputs and/or other non-visual communications for alarms and other miscellaneous functionalities.

In addition, in some implementations, the personal computing device 104 has built in accelerometers, heart-rate monitors and/or other electronic sensing devices that are able to monitor one or more conditions associated with the user or the user's environment.

In some implementations, such as the illustrated one, the glucose measuring device 102 and the personal computing device 104 are able to communicate with one another over a wireless communications channel. In some implementations, this functionality is achieved by virtue of a transceiver in the glucose measuring device 102 being able to communicate with a transceiver in the personal computing device 104. In some implementations, the glucose measuring device 102 (e.g., a CGM) has a transmitter that is able to send data to a receiver that can be plugged into the personal computing device (e.g., a phone).

In general, the system 100 tracks the user's actual blood glucose levels, enables the user to enter information into the personal computing device 104 about various glucose-affecting-events (e.g., consuming carbohydrates, receiving a bolus of insulin, changing an insulin basal rate or exercising) that will affect the user's blood glucose levels, and receive an accurate, timely estimated projection of the user's future blood glucose levels taking into account a relatively current actual value for the user's blood glucose level, from the glucose measuring device 102, and any recent events that may have an influence on the user's future blood glucose levels.

More particularly, the system 100 typically generates a plurality of estimated trajectories of the user's blood glucose level as influenced by one or more of the recent events and identifies which of the estimated trajectories represents a best fit to the actual blood glucose levels received from the blood glucose measuring device 102.

In a typical implementation, the estimated projection of the user's future blood glucose levels is presented as a curve (i.e., a future blood glucose curve) on the computer-based visual display of the personal computing device 104.

In addition, in some implementations, the system 100 presents the user with an indication of how accurate the estimated projection of the user's future blood glucose levels can be considered. In this regard, the system 100 may present, on the computer-based visual display of the personal computing device 104 an upper curve above the future blood glucose curve and a lower curve below the future blood glucose curve that collectively define a confidence band around the future blood glucose curve. In general, the width of the confidence band at each point in time reflects the degree of confidence that the system has in the estimated blood glucose level represented by the future blood glucose curve at that point in time.

Moreover, in some implementations, the system 100 is configured to derive from the historical blood glucose values and the glucose-affecting-events one or more therapeutic recommendations. These therapeutic recommendations can include, for example, recommendations to take a bolus on insulin (e.g., 2.5 units of insulin).

The system 100, in some implementations, also includes an insulin pump occlusion alarm. In a typical implementation, in order to detect whether the user's insulin pump may have an occlusion (e.g., a blockage that is preventing the delivery of dosed insulin to the user), the system 100 generates a first estimated trajectory (an all-events trajectory) of the user's blood glucose levels taking into account all of the recent events that may have an influence on the user's blood glucose levels and then generates a second estimated trajectory (a no-insulin trajectory) of the user's blood glucose levels excluding from consideration any recent events that relate to the user receiving a dose of insulin. Each trajectory is assigned a goodness-of-fit-metric by the system that assesses how well they model the historical glucose values. The system 100 compares the all-events trajectory to the no-insulin trajectory and, if the goodness-of-fit-metric of the no-insulin trajectory exceeds the goodness-of-fit-metric of the all-events trajectory by some threshold value, then the system 100 concludes that an occlusion exists. In some implementations, the system 100, upon making such a conclusion, triggers an alarm.

In various implementations, the personal computing device 104 can communicate either directly or via an indirect cloud-based server, for example, to a remote device, with some or all of the functionality in the personal computing device 104 being mirrored in the remote device. In some implementations, the alarm may include a text message sent either to the user's personal computing device 104 and/or to one or more other remote devices.

Figure 2:
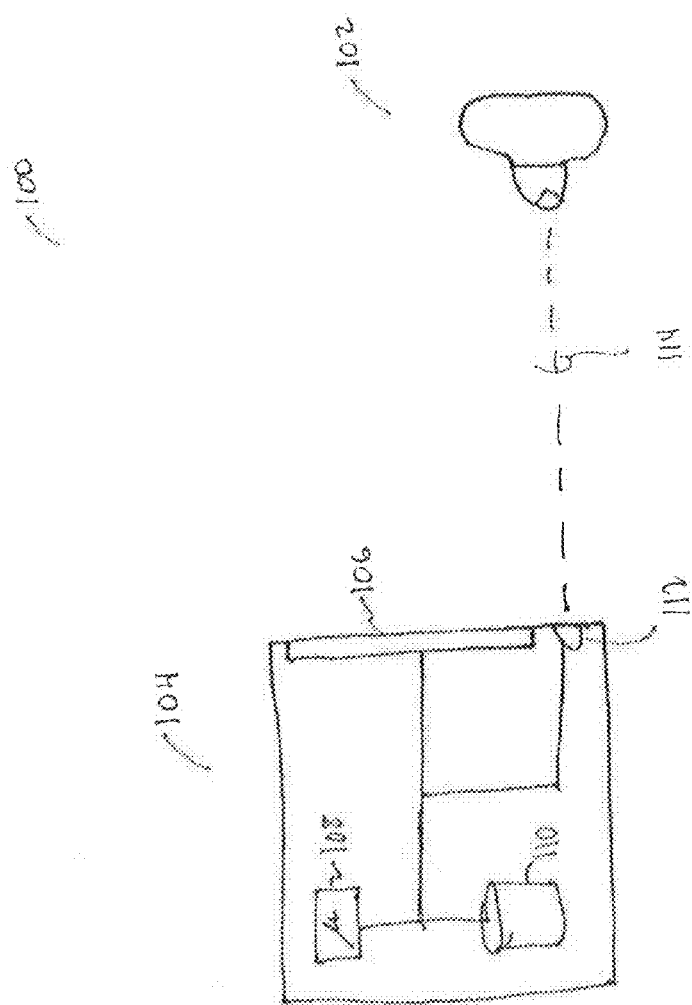
FIG. 2 is a schematic electrical diagram of the system in FIG. 1.

FIG. 2 is a schematic diagram showing various electrical components of the system 100 in FIG. 1.

According to the illustrated implementation, the personal computer device 104 has the touchscreen 106, as well as a computer-based processor 108, a computer-based memory 110 and a wireless transceiver 112. The touchscreen 106, the computer-based processor 108, the computer-based memory 110 and the wireless transceiver 112 are coupled to each other via internal communication lines.

In general, the computer-based processor 108 is configured to process data so as to facilitate various aspects of the functionalities disclosed herein. Moreover, in general, the computer-based memory 110 is configured to store data and software to facilitate various aspects of the functionalities disclosed herein.

The illustrated glucose measuring device 102 also has a wireless transceiver 114 that is adapted to communicate with the wireless transceiver 112 in the personal computer device 104 over a wireless communications channel 114. Alternatively, the glucose measuring device 102 has a transmitter that is adapted to communication with a receiver that plugs into the personal computer device 104.

Figure 3:
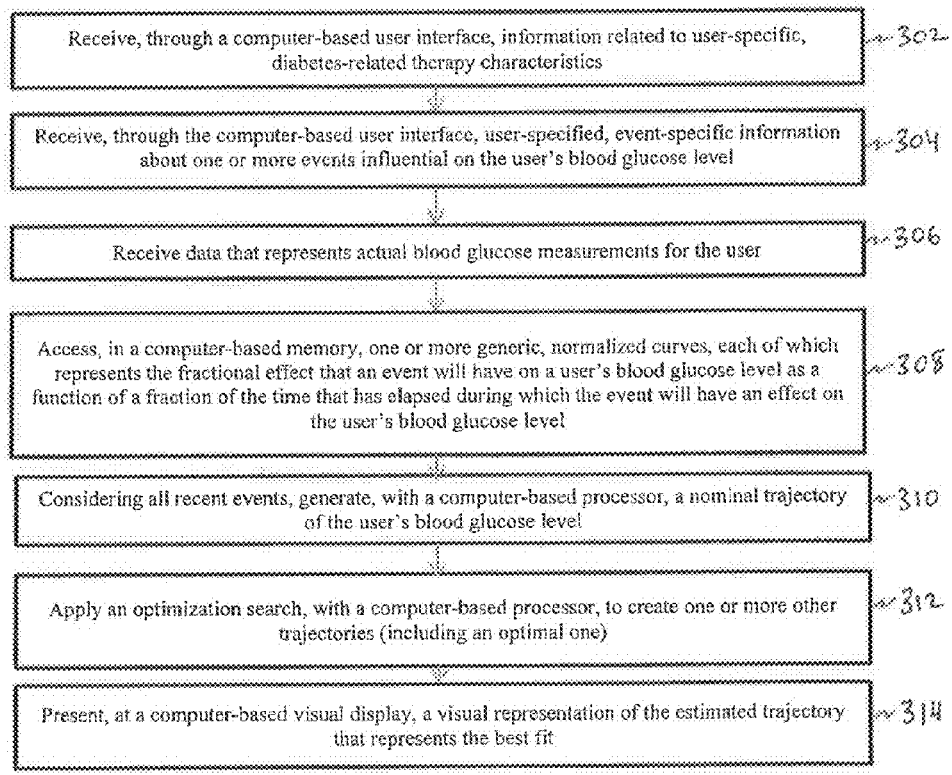
FIG. 3 is a flowchart of a process that can be performed in connection with the computer system of FIG. 1.

FIG. 3 is a flowchart showing an exemplary process performed by the personal computing device 102 of FIG. 1.

According the exemplary process, the personal computing device receives (at 302), through its computer-based user interface, information related to user-specific, diabetes related therapy characteristics. In a typical implementation, the user-specific, diabetes related therapy characteristics include a range of values for one or more of the following parameters: insulin-to-carbohydrate ratio, insulin sensitivity factor, duration of insulin action, time for carbohydrate absorption, duration of exercise effect, and ratio of exercise per hour to carbohydrates. In various implementations, other user-specific, diabetes related therapy characteristics (e.g., basal rate) may be received as well.

In general, the insulin-to-carbohydrate ratio indicates how many units of insulin a user is likely to need to take in order to "cover" a specified number of grams of carbohydrates. For example, if a user's insulin-to-carbohydrate ratio is 1:12, then that user will probably need 1 unit of insulin to offset every 12 grams of carbohydrates consumed. In general, the insulin sensitivity factor represents the amount that a user's blood glucose is lowered by the injection of 1 unit of insulin. In general, duration of insulin action or insulin action time is a measure of how long it will take a bolus or injection of insulin to lower a user's blood glucose level after the bolus or injection of insulin is given. In general, the time for carbohydrate absorption represents how long it will take for a quantity of carbohydrates to be fully absorbed by the user. In general, the duration of exercise effect is the amount of time that a certain amount of exercise will have an effect on the user's blood glucose level. In general, the ratio of exercise per hour to carbohydrates is the number of carbohydrates needed to offset the blood glucose lowering effect of one hour of exercise for the user.

FIG. 4 shows an exemplary screenshot 402 for entering this information.

The exemplary screenshot 402 includes a pair of data entry fields for each parameter. For each respective parameter, one of the data entry fields (labeled "low") allows the user to specify a lower end of a range for that parameter and the other data entry field (labeled "high") allows the user to enter an upper end of a range for that parameter.

In some implementations, the system 100 is adapted to present the user with the ability to specify a schedule of values for one or more of the parameters, where the values for one or more of the parameters can vary over time, for example, hour-to-hour or day-to-day.

In a typical implementation, the personal computer device 104 saves any and all user-specific, diabetes related therapy characteristics in the computer-based memory 110.

Referring again to FIG. 3, the illustrated process includes (at 304) receiving, through the computer-based user interface, user-specified, event-specific information about one or more events that are influential on the user's blood glucose level. Examples of events that are influential on the user's blood glucose level include: a consumption of carbohydrates, receipt of an insulin dose, or completion of exercise.

In some implementations, it is possible to pull the insulin and carb information from an insulin pump directly without requiring a user to enter the information. In addition, in some implementations, it is possible that exercise information is inferred from other sensor data as well (e.g., accelerometers, heart rate sensors, etc.).

The type of event-specific information that is received depends on the type of event, but, in general, for each event, it will include at least a time and quantity associated with the event. If, for example, a user takes 2 units of insulin (a first event) at about 8:00 am and then consumes a small sandwich, estimated to have about 24 grams of carbohydrates, between 8:00 am and 8:30 am (a second event), then the user might enter event-specific information indicating: (1) a dose of 2 units of insulin at 8:00 am, and (2) a consumption of 24 grams of carbohydrates at 8:15 am.

Figure 5:
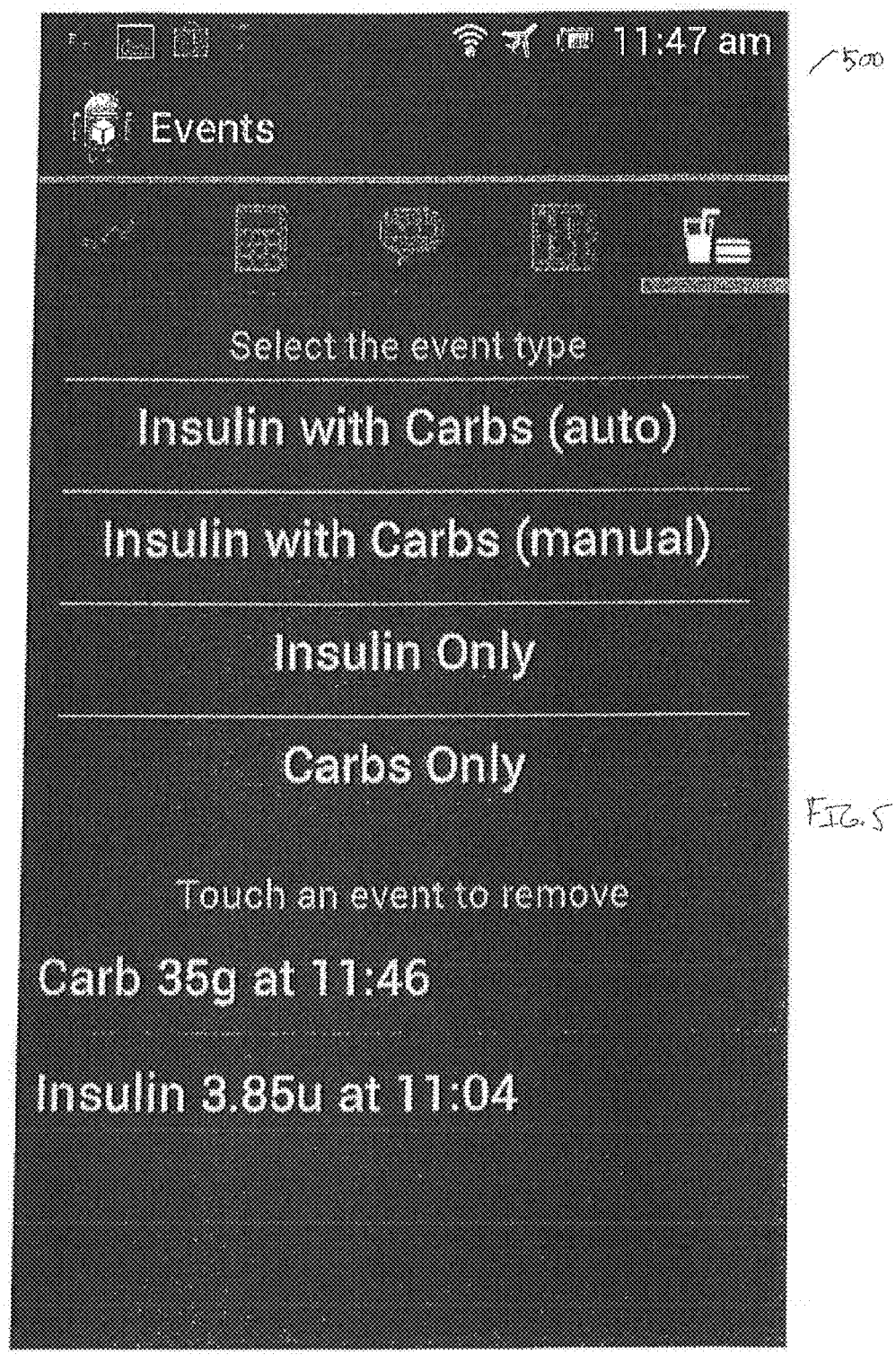
FIG. 5 is another screenshot that may appear on the personal computing device in FIG. 1.

FIG. 5 shows one implementation of a screenshot 500 that may be presented, for example, on the computer-based visual display of the personal computer device 104.

The illustrated screenshot 500 presents the user with four options for entering information about a specific event. The options include: "Insulin with Carbs (auto)," "Insulin with Carbs (manual)," "Insulin Only," and "Carbs Only." In other implementations, there may be other options including, for example, an exercise option.

If the user selects the "Carbs Only" option, for example, the personal computer device 104 prompts the user to specify event-specific information related to the user's consumption of carbohydrates. In a particular implementation, for example, the personal computer device 104 prompts the user to specify a time (or time period) at which the carbohydrates were consumed, and a quantity (e.g., an estimated number (or range) of grams of carbohydrates consumed).

If the user selects the "Insulin Only" option, for example, the personal computer device 104 prompts the user to specify event-specific information related to the a dose of insulin taken by the user. In a particular implementation, for example, the personal computer device 104 prompts the user to specify a time at (or time period within) which the dose was taken, and a quantity (e.g., an estimated number (or range) of units of insulin delivered).

In general, a change in insulin basal rate for the user may be represented by a sequence of discrete doses of insulin, where the sequence of discrete doses can be positive or negative depending on whether the change in insulin basal rate is an increase or decrease, respectively. In some implementations, the system 100 presents the user with the option of entering this type of information as well.

If the user selects the "Insulin with Carbs (manual)" option, for example, the personal computer device 104 prompts the user to specify event-specific information related to the user's consumption of carbohydrates, as well as event-specific information related to a dose of insulin taken by the user.

If the user selects the "Insulin with Carbs (auto)" option, for example, the personal computer device 104 prompts the user to specify event-specific information related to the a dose of insulin taken by the user. The personal computer device 104 then infers from the user's blood glucose level, as measured by the glucose measuring device 102, at the time of the event how much of the insulin administered was intended to treat a high blood sugar level and how much should be allotted to a consumption of carbohydrates.

The screenshot 500 also provides a listing, which appears near the bottom of the screen in the illustrated example, of recently-entered events-specific information. For example, the illustrated example lists recently entered event-specific information for two recently entries: "Carb 35 g at 11:46" and "Insulin 3.85 u at 11:04," respectively indicating that the user consumed 35 grams of carbohydrates at 11:46 and received 3.85 units of insulin at 11:04.

The listing is provided, at least in part, so that a user can review recent events that may be impacting or that may impact his or her blood glucose level. In addition, the screenshot includes functionality that enables the user to remove (or edit) any one of the listed events. As instructed on the screenshot 500, to do this, the user would simply "touch an event to remove," which typically would call up another screen or pop-up window asking the user to confirm or otherwise guiding the user to take appropriate steps to remove (or edit) the touched event.

In a typical implementation, the personal computer device 104 saves any and all event-specific information that the user enters in the computer-based memory 110.

Referring again to FIG. 3, according to the illustrated method, the personal computer device (at 306) receives data that represents actual blood glucose measurements for the user. In a typical implementation, the personal computer device 104 receives this data automatically from the blood glucose measuring device 102. This data may be transferred, for example, wirelessly from the blood glucose measuring device 102 on a somewhat regular or periodic basis. In some instances, at least some of the data that represents actual blood glucose measurements may be manually entered by a user after having measured his or her blood glucose level using a finger prick measuring system, for example.

Although this step (306) is shown as a discrete step in a sequence of steps in the illustrated flowchart, in a typical implementation, the personal computer device 104 receives actual blood glucose measurements from the blood glucose measuring device 102 at somewhat regular intervals and on an ongoing basis.

In a typical implementation, the personal computer device 104 saves the data that represents the actual blood glucose measurements over time in the computer-based memory 110.

According to the illustrated method, the computer-based processor 108 of the personal computer device 104 generates (at 308, 310 and 312) a plurality of estimated trajectories of the user's blood glucose level as influenced by one or more events, for which the user has entered event-specific information, and identifies which of the estimated trajectories represents a "best fit" to the set of data that represents the actual blood glucose measurements for the user.

Figures 6A, 6B:
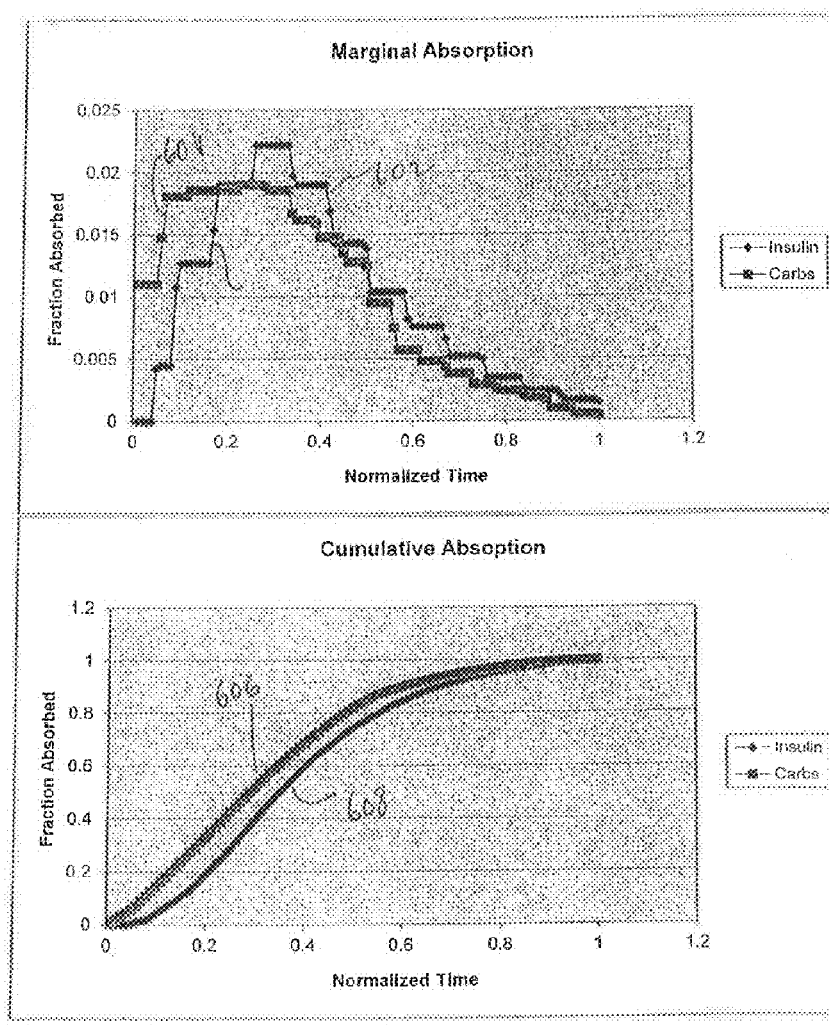
FIG. 6A includes a graph that represents a generic, normalized, marginal absorption of insulin and carbohydrates over time.
FIG. 6B includes a graph that represents a generic, normalized, cumulative absorption of insulin and carbohydrates over time.

More particularly, according to the illustrated flowchart, the computer-based processor 108 accesses (at 308), typically from the computer-based memory 110, one or more generic, normalized curves, each of which represents the fractional effect that a specific type of event (e.g., a consumption of some quantity of carbohydrates, a dose of some quantity of insulin, etc.) will have on a user's blood glucose level as a function of the amount of time elapsed, expressed as a fraction of total time that the event is expected to have an effect on the user's blood glucose level. FIG. 6A and FIG. 6B show some examples of generic, normalized curves that include this type of information.

In FIG. 6A, for example, there are two curves—one (602) is a generic, normalized curve showing the marginal absorption of a dose of insulin over time and the other (604) is a generic, normalized curve showing the marginal absorption of quantity of carbohydrates over time.

In general, the insulin marginal absorption curve (602) represents what fraction of a dose of insulin is absorbed during each one of a plurality of discrete time periods over the course of a normalized period of time. Moreover, the generic, normalized marginal insulin absorption curve provides a general shape of insulin action in a user, which the personal computer device 104 can use to help determine the effect that an actual dose of insulin (e.g., 2 units) will have on a user's blood glucose level. More particularly, the personal computer device is able to parameterize the action of the dose of insulin based on the event's start time, magnitude (e.g., number of units received) and duration of action, while keeping the overall shape of the generic insulin absorption curve relatively constant. In this regard, the percentage of insulin absorption is generally treated as constant for a given fraction of the total absorption time, regardless of how long the full absorption time is. For example, if an insulin event has a total duration of 6 hours and after 2 hours the percentage of absorption is 40%, then in another scenario where the total duration of action is 3 hours, the curve would indicate a 40% absorption after 1 hour has passed.

Other examples of this type of information are available. See, e.g., "Effect of Age of Infusion Site and Type of Rapid-Acting Analog on Pharmacodynamic Parameters of Insulin Boluses in Youth With Type 1 Diabetes Receiving Insulin Pump Therapy" by Swan, Dziura et al, which is incorporated by reference herein.

In general, the carbohydrate marginal absorption curve (604) represents the fraction of carbohydrates consumed is absorbed during each one of a plurality of discrete time periods over the course of a normalized period of time.

The rate at which carbohydrates affect blood glucose can be highly variable and may be affected by the type of carbohydrate as well as what else is consumed along with the carbohydrates, such as protein and fat. That is, the consistency of the meal can have a marked impact on how quickly carbohydrates are absorbed in the gut. This is a vexing problem for insulin dependent diabetics and one that the techniques disclosed herein can be quite helpful in solving. Although the speed of the carbohydrate absorption is highly variable, the shape of the carbohydrate action curve tends to be relatively stable with the shape showing, in general, a monotonic increase after ingestion to a peak at some subsequent point. After the maximum absorption crest the carbohydrate absorption profile generally follows a monotonic decreasing function until the action tails off asymptotically to zero.

Note that while it may not be possible to know the exact profile of a carbohydrate event's absorption profile, the personal computer device 104 can use the knowledge that the shape of the profile is somewhat generic and use estimates of the start time, length and magnitude of the carbohydrate's action to estimate how the carbohydrates are absorbed by the user. To this end, the personal computer device can use a generic mixed-meal carbohydrate absorption curve for modeling the shape of glucose absorption associated with carbohydrate consumption. There are many such curves in the literature and while the model outputs may be marginally affected by the choice of the curve, the overall function of the system is not greatly affected by this choice.

Other examples of this type of information are available. See, e.g., "Insulin Administration and Rate of Glucose Appearance in People with Type 1 Diabetes" by Pennant, Mary et al, which is incorporated by reference herein.

Similar to the insulin absorption curve, the personal computer device 104 can parameterize the carbohydrate absorption curve based on start time, duration of action and magnitude. However, the system 100 considers that the percentage of carbohydrate absorption is constant for a given fraction of the total absorption time, regardless of how long the full absorption time is. Thus, if a 4-hour carbohydrate event has 60% of its absorption completed after 2 hours, another 2 hour carbohydrate event will have 60% of its absorption completed after only 1 hour.

In FIG. 6B there are two curves—one (608) is a generic, normalized curve representing the cumulative absorption of insulin over time and the other (606) is a generic, normalized curve representing the cumulative absorption of carbohydrates over time.

In general, the insulin cumulative absorption curve (608) represents the fractional cumulative absorption of a dose of insulin at each point in time over the course of a normalized period of time. Moreover, in general, the carbohydrate cumulative absorption curve (606) represents the fractional cumulative absorption of carbohydrates at each point in time over the course of a normalized period of time.

In a typical implementation, the personal computer device 104 stores curves like one or more of the curves 602-608 and also stores similar curves that represent the marginal and/or cumulative impact of some amount of exercise over a normalized period of time.

In essence, the generic, normalized curves include information (e.g., a generic curve shape representing future absorption/impact) that facilitates modeling the effects that one or more of the events may have on the user's future blood glucose. Moreover, it includes information that, in consideration of other parameters, enables the system to estimate how much carbohydrates and/or insulin a user has in his or her body at specific points in time that is yet to be absorbed. These concepts can be referred to as carbs-on-board or insulin-on-board.

Referring again to FIG. 3, according to the illustrated method, considering all recent events, the computer-based processor 108 (at 310) generates a nominal trajectory of the user's blood glucose level. In some implementations, the computer-based processor 108 accomplishes this by parameterizing one or more of the generic, normalized curves with the entered specifics of the glucose-affecting-events. The nominal trajectory generally uses the midpoint of all diabetes therapy related parameter ranges to turn the generic, normalized curves into actual blood glucose trajectories.

The computer-based processor 108 (at 312), then applies an optimization search such as a gradient descent or a genetic algorithm to create one or more other trajectories, including an optimal trajectory. In a typical implementation, the optimization search iterates to create a plurality of new trajectories until it converges on a solution that it deems optimal, given the search stopping constraints. The search stopping constraints generally define where the iterative optimization searching should stop. Each solution (including the optimal one) generally consists of a set of parameters, including the user-specific, diabetes-related therapy parameters and specifics for each glucose-affecting-event, that may be applied to the generic, normalized curves to create actual glucose trajectories of the user's blood glucose levels In a typical implementation, the nominal trajectory is a base trajectory and at least one of the one or more other trajectories will be considered by the personal computer device 104 to be a better estimate (i.e., an optimization) of the user's actual blood glucose levels.

Many of the parameters that the personal computer device uses to construct the nominal trajectory and the one or more other trajectories have limited accuracy. This is because the parameters are based on estimates only and/or may be based on one or more other factors.

For example, the magnitude (e.g., number of grams) of carbohydrates consumed by a user is usually just an estimate. Literature suggests that users are prone to misestimate the amount of carbohydrates that are consumed in a given event by up to 30%. Users also misestimate the amount of insulin delivered in a given event, especially when taken by manual injection. In addition, in almost all cases, the duration of absorption of carbohydrates is an estimate.

The parameters that may be affected by one or more other factors include, for example, the duration (i.e., the speed of action) associated with a dose of insulin, which can vary as a result of many factors such as location of injection, exercise, activity or temperature after injection, or length of time that an insulin pump infusion site has been attached. In addition, the exact same meal and bolus regimen can have varied effects in the same person at the same time on different days as a result of exogenous physiological factors such as stress or menstruation.

Moreover, given their nature, the different parameters may have different degrees of accuracy. For example, although users are prone to misestimate the amount of carbohydrates that are consumed in a given event by up to 30%, typically a user's estimate of insulin delivered is far more accurate than +/−30%, because the syringes used to deliver doses of insulin are usually relatively precise.

In a typical implementation, the personal computer device 102 takes into account the limited accuracy of the different parameter values by implicitly acknowledging that one or more of the parameters (or all of the parameters) are estimates and, therefore, may vary from the values entered. Rather than forcing those parameters to be fixed, the personal computer device 102 allows for a range of values (that may be entered by the user or otherwise established by the personal computer device 104 typically around whatever value has been entered) for each parameter. In addition, for parameters where no value is given, such as carbohydrate absorption time, the personal computer device 102 generally provides a wide range of parameter values.

In a typical implementation, the computer-based processor 108 generates the nominal trajectory of the user's blood glucose level by utilizing a value for each parameter that is either: (1) the exact single value that was entered for that parameter or, (2) if the parameter has an associated range of values, a mid-point (or approximate mid-point) of the range for that parameter. In general, the computer-based processor generates the nominal trajectory by parameterizing one or more of the generic, normalized curves based on start time, duration of action and magnitude. This can be represented formulaically by the following formulas.

$$G\_j = G\_r + \text{insulin\_delta} + \text{carb\_delta} \quad (1)$$

Insulin_delta=mult*Sum_insulin_events[−ISF*
  [($INA\_j\_e - INA\_r\_e$)*$I\_e$]]
Carb_delta=mult*Sum_carbohydrate_events[$ISF/CR$*
  [($CNA\_j\_e - CNA\_r\_e$)*$C\_e$]]
Mult=1 where $j >= r$, −1 where $j < r$
where,
G_j is the blood glucose at time j
G_r is the blood glucose at reference time r ISF is the insulin sensitivity factor ((mg/dl)/Unit)
CR is the carbohydrate to insulin ratio (grams/Unit)
INA_i_e is the cumulative normalized absorption value for insulin event e at time i
CNA_i_e is the cumulative normalized absorption value for carbohydrate event e at time i
I_e is the magnitude of insulin event e
C_e is the magnitude of carbohydrate event e
Mult is a the sign of the change relative to reference time In one embodiment of the system, the current time (i.e., whatever time the calculations are being performed) is the reference point and the curve produced describe how the blood glucose varies before and after the reference point. In various implementations, the ISF and the CR may have schedules for different times in the day or week.

Then, the computer-based processor 108 generates the one or more other trajectories by changing the value of one or more of the parameters from the values that were used to generate the nominal trajectory, with the aim of achieving a better fit between the solutions represented by the one or more other trajectories relative to the actual blood glucose measurements received from the blood glucose measuring device 104.

The computer-based processor (at 312) identifies which of the estimated trajectories represents a "best fit" to the set of data that represents the actual blood glucose measurements for the user. There are a variety of techniques available to assess how good a "fit" each solution (i.e., the nominal trajectory and each of the one or more other trajectories) is to the actual blood glucose measurements. According to one method, the computer-based processor 108 assesses how closely the prior glucose values match the actual historical glucose values provided by the glucose sensing device. This may be calculated by averaging the absolute difference between the solution's historical blood glucose values and the actual historical blood glucose values at different points in time. In general, the smaller this difference is, the better the solution.

A further metric of how good a "fit" each solution is, which may be combined with the sum of the absolute differences discussed above, is the similarity of the first and/or second derivatives of the two blood glucose curves. By including one or both of these derivatives into the assessment of the solution's quality, the algorithm may provide more accurate predictions of future levels, especially when the absolute value of the near term second derivative of the historical glucose values is large. Those skilled in the art will understand that there are many more ways of assessing how good a "fit" a particular solution is and optimizing the personal computer device's 104 ability to quickly arrive at an optimized (i.e., satisfying a threshold degree of fitness) solution relative to the actual, measured historical blood glucose values. The foregoing techniques are provided as examples only.

In general, the optimization problem (i.e., trying to reach a solution that satisfies a threshold degree of fitness relative to the actual, measured historical blood glucose values) is non-linear and thus requires heuristic, stochastic or iterative methods to be used to find local maximum solutions. One embodiment of the personal computer device 104 uses genetic algorithms to search the solution space for good solutions. Another uses simulated annealing, a type of genetic algorithm to search the solution space. While these search methods are robust and certainly feasible, they are computationally-intensive and non-deterministic, therefore, may be deemed to have somewhat limited utility, especially in an interactive, portable system intended to provide therapeutic recommendations to a user.

A further embodiment employs the insight that although the solution space is generally very large, a gradient descent algorithm seeded with the midpoint of the constrained range for each parameter should do a reasonably good job of finding a good solution. This approach has the benefit of being very computationally efficient, deterministic and generally only diverges from the input-estimates insofar as it improves the solution.

It may be instructive to consider a few specific examples of how the personal computer device 104 handles different scenarios.

Scenario 1:

According to scenario 1, the personal computer device 104 receives the following specific estimates of diabetes related therapy parameters:
Insulin-to-carb ratio (CR)=[14, 16] grams/unit
Insulin sensitivity factor (ISF)=[45,55] mg/dl/unit
Duration of insulin action (DIA)=[4, 5] hours
Range of carbohydrate action=[2, 6] hours In addition, the personal computer device 104 receives the following user-entered event information:
Event type: Carbohydrate only
Time: 8:00
Quantity: 30 grams The computer-based processor 108 generates a nominal trajectory that uses the exact value entered or the midpoint (or approximate midpoint) where a range of values has been provided for the parameters. So:
CR=15 grams/unit
ISF=50 mg/dL/unit
Carb Action=4 hrs
Start Time=8:00
Quantity=30 grams Then, the computer-based processor 108 generates an optimized trajectory (among one or more other trajectories), where the optimized parameterization ends up being:
CR=15 grams/unit
ISF=50 mg/dL/unit
Carb Action=2.2 hrs
Start Time=8:25
Quantity=35.5 grams The optimization is run at approximately 9:00, one hour after the event (i.e., consuming a quantity of carbohydrates) occurred. The optimization found that the most likely scenario was that the carbohydrates had a faster action that the nominal (2.2 vs. 4 hrs) and that the quantity was likely greater than the user entered (35.5 vs. 30 grams). In addition, the likely start time was found to be later than the user entered (8:25 vs. 8:00). At 9:00, the carbs-on-board for the nominal profile is less than the optimized profile's carbs-on-board (17.9 vs. 19.8 grams) showing that the optimal profile holds an estimate of more carbs remaining to be digested than the nominal originally had suggested.

Figure 7A:
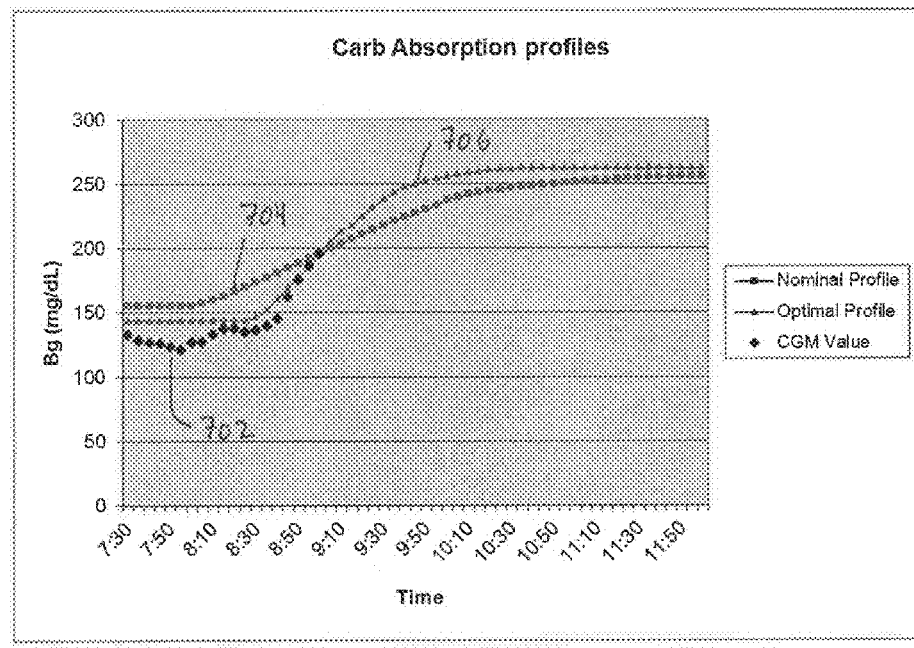
FIG. 7A includes a graph that represents actual blood glucose values, a nominal profile of estimated future blood glucose levels and an optimal profile of estimated blood glucose levels over time.

FIG. 7A is a chart that includes three curves that represent blood glucose values (in mg/dL) vs. time related to scenario 1.

In particular, the illustrated chart has: a first curve 702 showing a plot of actual, measured blood glucose levels that have been received from a continuous glucose monitor, a second curve 704 showing a plot of the nominal trajectory of blood glucose values calculated by the computer-based processor 108, and a third curve 706 showing the optimal one of the one or more other trajectories calculated by the computer-based processor 108.

A cursory review of the optimal trajectory curve 706 reveals that it is, indeed, a closer fit to the actual measured blood glucose curve 702 than the nominal blood glucose curve 704.

Since the computer-based processor 108 has access to information related to the user's actual blood glucose levels, any carbohydrates the user has consumed, how those carbohydrates will be absorbed, etc., the computer-based processor 108 can estimate the quantity of carbs-on-board for the user at any point in time after the consumption. Carbs-on-board refers to the quantity of carbohydrates in the user's system that has yet to be fully absorbed.

Figure 7B:
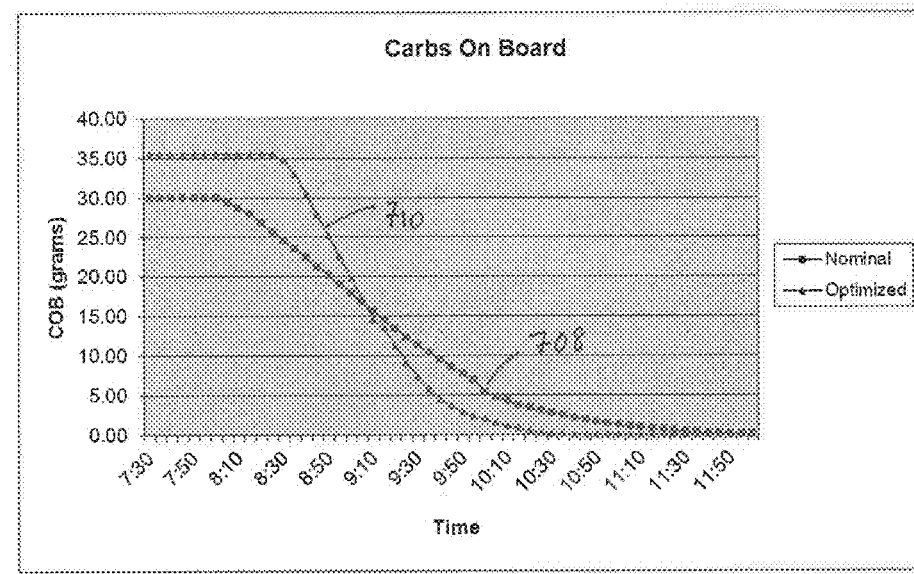
FIG. 7B includes a graph that represents a nominal profile of carbs-on-board and an optimized profile of carbs-on-board over time.

FIG. 7B is an example of a chart that includes a plot of the user's estimated carbs-on-board over time based on the scenario in FIG. 7A. As mentioned above, the user's estimated carbs-on-board at any point in time can be derived based on the parameters entered and the curves (or other information) showing how a unit quantity of carbohydrates is absorbed by the user. The user's estimated insulin-on-board at any point in in time can be derived in a similar manner.

The illustrated chart has two curves: a first curve 708 showing a nominal trajectory of carbs-on-board estimates, and a second curve 710 showing an optimal trajectory of carbs-on-board estimates. In a typical implementation, the nominal trajectory (curve 708) is generated using information that was used to generate the nominal blood glucose trajectory 704 in FIG. 7A. Moreover, in a typical implementation, the optimal trajectory (curve 710) is generated using information that was used to generate the optimized blood glucose trajectory 706 in FIG. 7A. Similarly, the computer-based processor 108, in various implementations, generates insulin-on-board trajectories, nominal and optimized.

As discussed herein, carbs-on-board and insulin-on-board predictions can facilitate providing therapeutic recommendations, trigger alarms, etc.

Scenario 2:

According to scenario 2, the personal computer device 104 receives the following specific estimates of diabetes related therapy parameters:

Insulin-to-Carb ratio (CR)=[14, 16] grams/unit
Insulin sensitivity factor (ISF)=[45,55] mg/dl/unit
Duration of insulin action (DIA)=[4, 5] hours
Range of carbohydrate action=[2, 6] hours In addition, the personal computer device 104 receives the following user-entered event information:

Event type: Carbohydrate and Insulin
Time of carbohydrate consumption: 8:30
Quantity of carbohydrate consumption: 50 grams
Time of insulin dose: 8:30
Quantity of insulin dose: 2.5 units The computer-based processor 108 generates a nominal trajectory that uses the exact value entered or the midpoint (or approximate midpoint) where a range of values has been provided for the parameters. So:

CR=15 grams/unit
ISF=50 mg/dL/unit
Carb Action=4 hrs
Carb Start Time=8:30
Carb Quantity=50 grams
DIA=4.5 hrs
Insulin Start Time=8:30
Insulin Dose=2.5 Units Then, the computer-based processor 108 generates an optimized trajectory (among one or more other trajectories), where the optimized parameterization ends up being:

CR=15 grams/unit
ISF=50 mg/dL/unit
Carb Action=2.9 hrs
Start Time=8:22
Carb Quantity=58 grams
DIA=4.9 hrs
Insulin Dose=2.5 Units The optimization is run at 10:30, approximately two hours after the events occurred. The optimization found that the most likely scenario was that the carbohydrates had a faster action that the nominal profile (2.9 vs. 4 hrs) and that the quantity of carbohydrates was likely greater than what the user entered (58 vs. 50 grams). In addition, the carbohydrates start time was found to be earlier than the user entered (8:22 vs. 8:30). Carbs-on-board for the nominal profile was found to be greater than the optimized profile's carbs on board (8.95 vs. 2.79 grams). The DIA for the optimized profile is 4.9 vs. 4.5 hrs for the nominal profile. As a result, the IOB for the optimized profile is 1.01 vs. 0.85 units for the nominal profile.

FIG. 8A is a chart that includes three curves that represent blood glucose values (in mg/dL) vs. time related to scenario 2.

In particular, the illustrated chart has: a first curve 802 showing a plot of actual, measured blood glucose levels that have been received from a continuous glucose monitor, a second curve 804 showing a plot of the nominal trajectory of blood glucose values calculated by the computer-based processor 108, and a third curve 806 showing the optimal one of the one or more other trajectories calculated by the computer-based processor 108.

A cursory review of the optimal trajectory curve 806 reveals that it is, indeed, a closer fit to the actual measured blood glucose curve 802 than the nominal blood glucose curve 804.

FIG. 8B is an example of a chart that includes a plot of the user's estimated carbs-on-board based on the scenario in FIG. 8A.

More particularly, the illustrated chart has two curves: a first curve 808 showing a nominal trajectory of carbs-on-board estimates, and a second curve 810 showing an optimal trajectory of carbs-on-board estimates. In a typical implementation, the nominal trajectory (curve 808) is generated using information that was used to generate the nominal blood glucose trajectory 804 in FIG. 8A. Moreover, in a typical implementation, the optimal trajectory (curve 810) is generated using information that was used to generate the optimized blood glucose trajectory 806 in FIG. 8A. Similarly, the computer-based processor 108, in various implementations, generates insulin-on-board trajectories, nominal and optimized.

Referring again to FIG. 3, according to the illustrated method, the computer-based processor 108 presents (in 314) at the personal computer-based display, a visual representation of the estimated trajectory that represents the best fit.

Figure 9A:
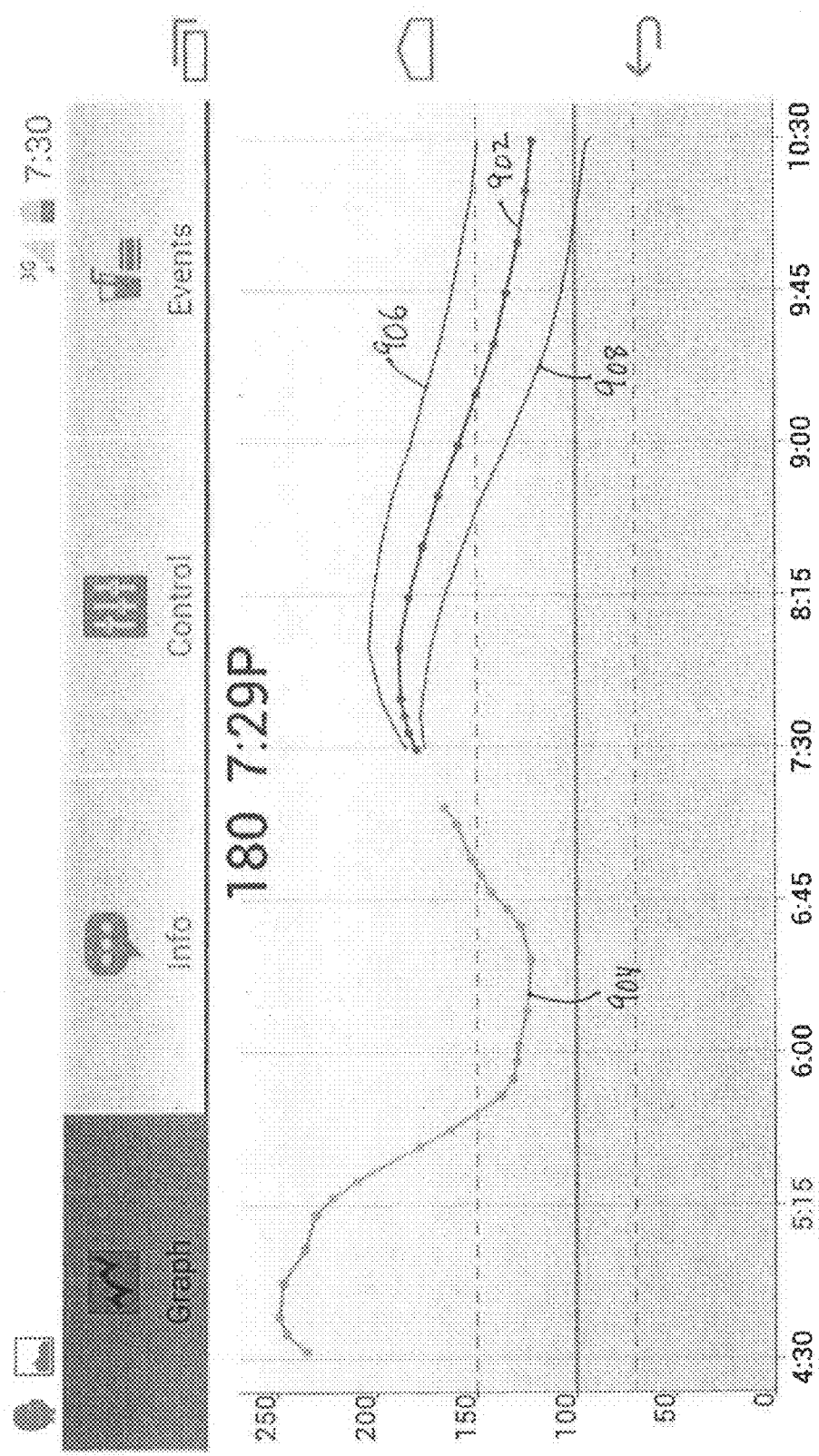
FIG. 9A is a screenshot that may appear on the personal computing device in FIG. 1 and that includes an optimal profile (trajectory) of estimated blood glucose levels over time and other information.

An example of a screenshot that includes the visual representation of the estimated trajectory that represents the best fit is provided in FIG. 9A.

In the illustrated screenshot, the visual representation of the estimated trajectory that represents the best fit is a curve 902 that extends from about 7:29 PM (current time in the illustrated example) forward until approximately 10:30 PM.

The illustrated screen shot also includes a historical curve 904 of blood glucose values. In a typical implementation, the historical curve 904 represents actual measured blood glucose values received, for example, from a continuous glucose monitor.

The illustrated screen shot also include an upper curve 906 and a lower curve 908 that collectively define a boundary around the best fit trajectory 902.

In general, the upper curve 906 and the lower curve 908 provide the user of the system with a notion of how accurate the projected trajectory can be expected to be. In general, the narrower the boundary at a particular point in time, the more accurate the projected trajectory can be expected to be at that point in time. Additionally, the broader the boundary at a particular point in time, the less accurate the projected trajectory can be expected to be at that particular point in time.

The boundary can be established in a variety of possible ways. One way is to shift the values of the parameters associated with the optimal trajectory together toward either faster, greater glucose variation on the one hand and longer, lesser glucose variation in the other hand. The degree of the shift for each respective parameter value should be related to the confidence of the original estimate and often is proportional with the amount that the variable is allowed to vary within the constraints of the original optimization. By examining the two variants (both the greater and lesser variations), the computer-based processor 108 can provide the user with a sense for how much confidence he or she can have in the optimal trajectory.

In other implementations, the boundary can be established by focusing on a subset of the parameters. In particular, the length and magnitude of the carbohydrate events tend to create the most variation in the system outputs and thus varying only those parameters may provide good results for the upper curve 906 and the lower curve 908 with less computational effort.

In general, and as illustrated in the exemplary screenshot of FIG. 9A, the distance between the upper and lower curves 906 and 908 and, therefore, the width of the boundary around the optimal trajectory curve 902 increases over time. This reflects the general idea that the farther out in time that a projected value is, the less accurate that projection can be expected to be.

Figure 9B:
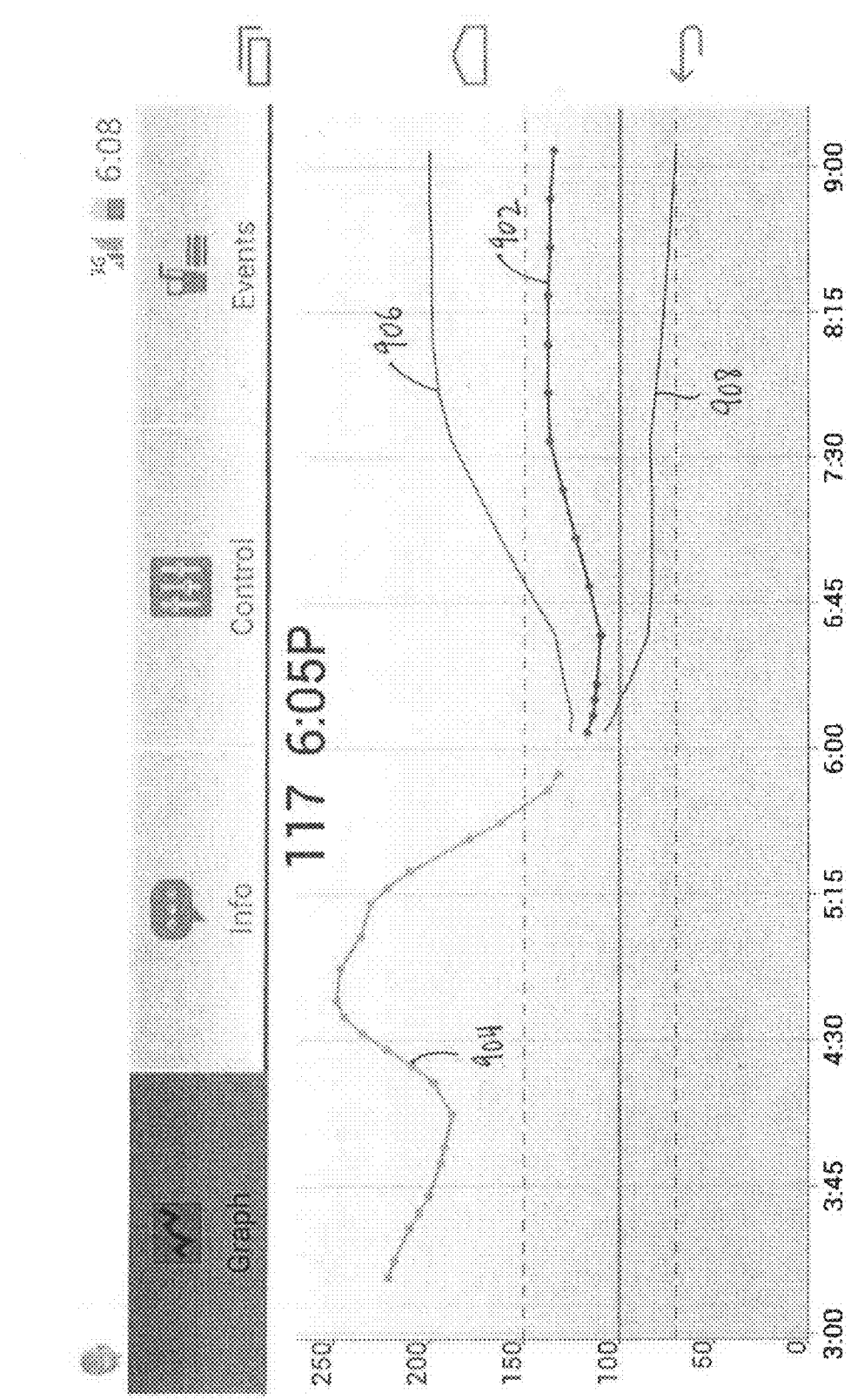
FIG. 9B is a screenshot that may appear on the personal computing device in FIG. 1 and that includes an optimal profile (trajectory) of estimated blood glucose levels over time and other information.

The screenshot in FIG. 9B is similar to the screenshot in FIG. 9A. However, the boundary defined by the upper curve 906 and the lower curve 908 in FIG. 9B is generally larger in FIG. 9B than it is in FIG. 9A, thus indicating a lower level of confidence in the accuracy of the best fit trajectory curve 902 in FIG. 9B.

In some implementations, the system 100 includes a bolus calculator that leverages information produced using the techniques disclosed herein. More particularly, armed with the IOB and COB values, the computer-based processor 108 can act as a calculator that takes a current blood glucose value and a planned carbohydrate ingestion amount and provides a recommended dose of insulin (i.e., a bolus). The current blood glucose value may be input by the user or may be transmitted directly from a glucose sensing device (e.g., a CGM or blood glucose fingerstick meter).

In one implementation, the calculation of the insulin bolus, which may be performed by the computer-based processor 108, is as follows:

Carb_contribution=carbs/*CR*

Bg_Contribution=(*BG*−target_*BG*)\**ISF*

$$\text{Insulin Bolus calculation} = \text{Carb\_contribution} + BG\_\text{Contribution} - IOB + COB/CR \quad (2)$$

Where,
carbs=the carbs to be ingested at the time (this can be 0 in non-prandial conditions)
CR=Carbohydrate ratio (grams/Unit)
BG=current blood glucose value (mg/dL)
Target_BG=desired target BG value–static parameter set by user (mg/dL)
ISF=Insulin sensitivity factor ((mg/dL)/Unit)
IOB=Insulin-On-Board–the sum of all insulin events future absorption (Units)
COB=Carbs-On-Board–the sum of all carb events future absorption (grams)

The bolus calculator can run in real-time and on a substantially continuous basis. It can provide near instantaneous and regular recommendations to the user of what corrective action it recommends to improve future blood glucose levels proximity to target blood glucose level. In some implementations, if the calculation is a positive number, it indicates a further amount of insulin is required; if the calculation is a negative number, it indicates a further amount of carbohydrates are needed and those can be computed by multiplying the result by −CR.

The COB and IOB used in the bolus calculator may be derived from the optimal solution, from one of the upper or lower bounding solutions described above, or from some weighted average of any two of the solutions depending, for example, on how aggressive the user desires to be. In addition, the output of the bolus calculator may be displayed in simple text format to provide a current recommendation to the patient.

Figure 10:
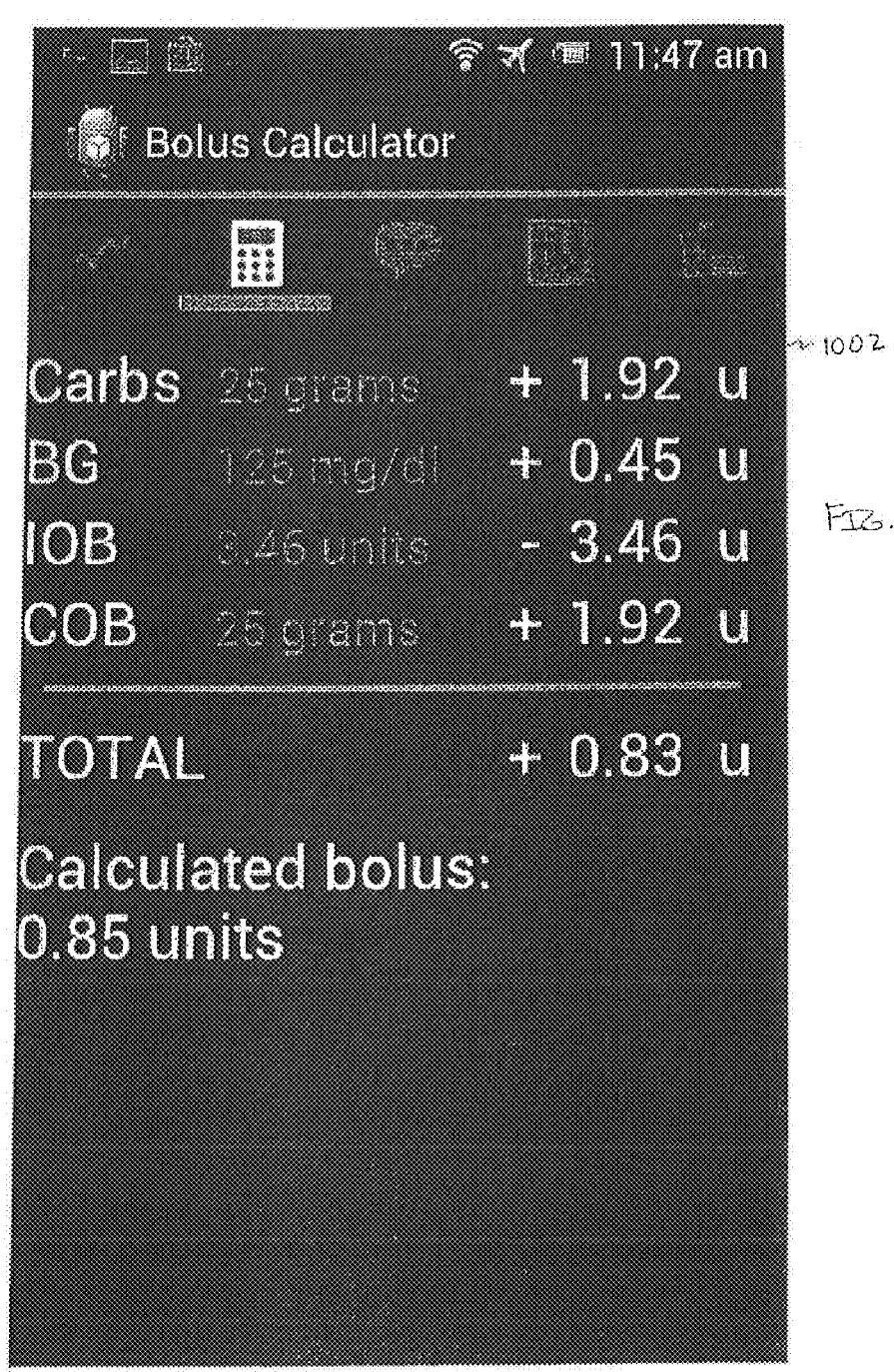
FIG. 10 is a screenshot that may appear on the personal computing device in FIG. 1 and that includes a representation of some functionality associated with a bolus calculator.

FIG. 10 is screenshot of an exemplary bolus calculation screen 1002 that may appear on the visual display of the personal computing device 104.

According to the illustrated example, the carbs (e.g., the quantity of carbs about to be consumed by the user) is estimated to be 25 grams, the user's current blood glucose level (based on information received from the glucose monitoring device 102) is estimated to be 125 mg/dl, the insulin-on-board (IOB) is 3.46 units (determined, for example, in connection with the optimal trajectory of the user's blood glucose levels), the carbohydrates-on-board (COB) is 25 grams (determined, for example, in connection with the optimal trajectory of the user's blood glucose levels).

The system 100 assigns a unit value of insulin to offset each of the values identified. For example, according to the illustrated example, +1.92 units of insulin would offset the 25 grams of carbs about to be consumed, +0.45 units of insulin would offset the 125 mg/dl current blood glucose level, —3.46 units of insulin would offset the 3.46 units of insulin-on-board (IOB) and +1.92 units of insulin would offset the 25 grams of carbs-on-board (COB). The units of insulin to offset the IOB is a negative number, because insulin has the effect of tending to decrease (not increase) a user's blood glucose level.

The system 100 sums up the units of insulin that would offset the effects of carbs about to be consumed, the current blood glucose level, the IOB and the COB. The total, recommended bolus, based on this calculation is +0.83 units of insulin.

Figure 11:
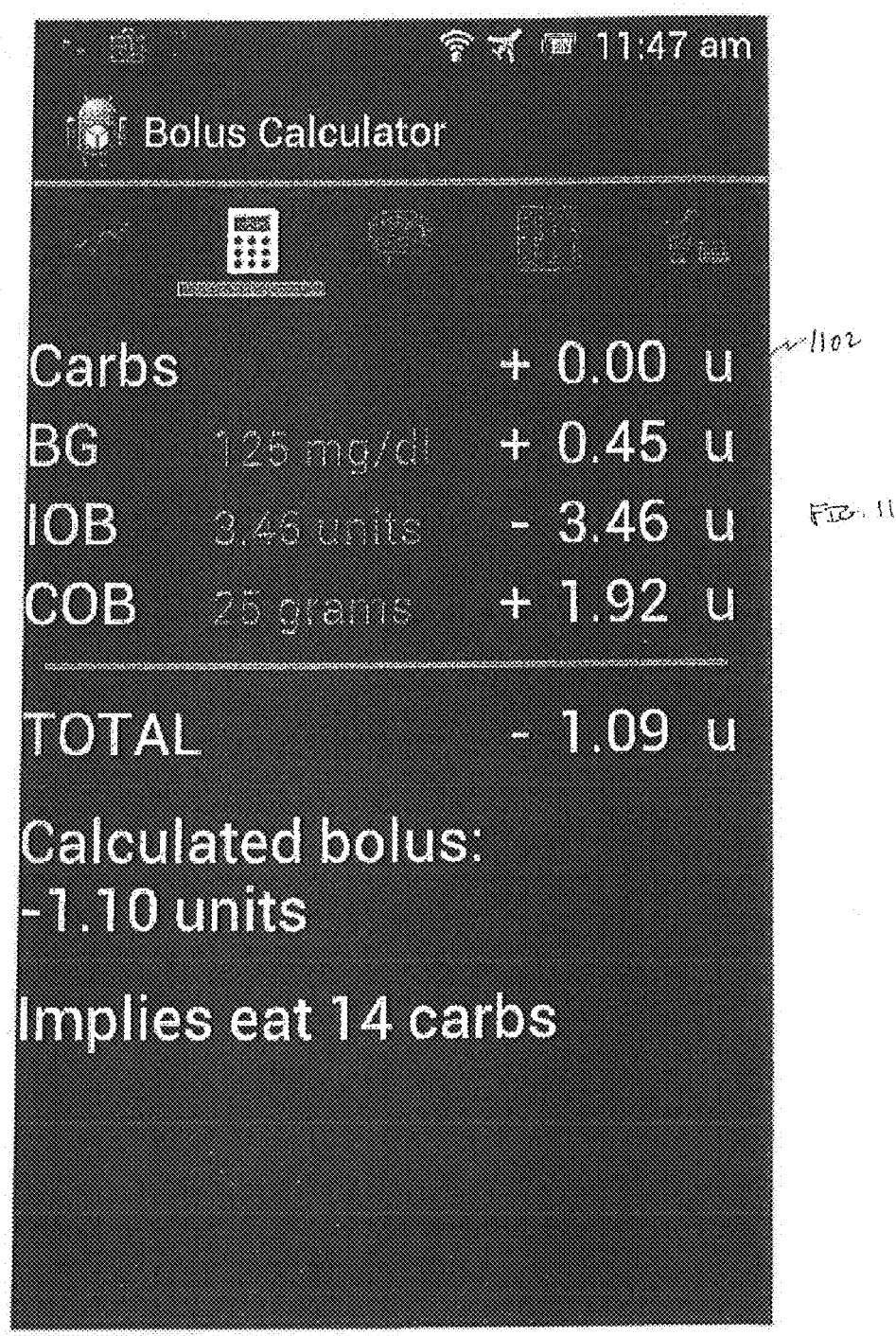
FIG. 11 is a screenshot that may appear on the personal computing device in FIG. 1 and that includes a representation of some functionality associated with a bolus calculator.

FIG. 11 is screenshot of another exemplary bolus calculation screen 1102 that may appear on the visual display of the personal computing device 104.

According to the illustrated example, the carbs (e.g., the quantity of carbs about to be consumed by the user) is not specified, the user's current blood glucose level (based on information received from the glucose monitoring device 102) is estimated to be 125 mg/dl, the insulin-on-board (IOB) is 3.46 units (determined, for example, in connection with the optimal trajectory of the user's blood glucose levels), the carbohydrates-on-board (COB) is 25 grams (determined, for example, in connection with the optimal trajectory of the user's blood glucose levels).

The system 100 assigns a unit value of insulin to offset each of the values identified. For example, according to the illustrated example, +0.45 units of insulin would offset the 125 mg/dl current blood glucose level, −3.46 units of insulin would offset the 3.46 units of insulin-on-board (IOB) and +1.92 units of insulin would offset the 25 grams of carbs-on-board (COB). The units of insulin to offset the IOB is a negative number, because insulin has the effect of tending to decrease (not increase) a user's blood glucose level.

The system 100 sums up the units of insulin that would offset the effects of carbs about to be consumed, the current blood glucose level, the IOB and the COB. The total, recommended bolus, based on this calculation is −1.09 units of insulin. The negative value here would suggest to the user that the recommended therapy is to consume 14 carbohydrates to offset the excess of −1.09 units of insulin found in the calculation. The 14 carbohydrates are computed by multiplying 1.09 by the carbohydrate to insulin ratio of approximately 13 and then rounding to the nearest integer.

Figure 12:
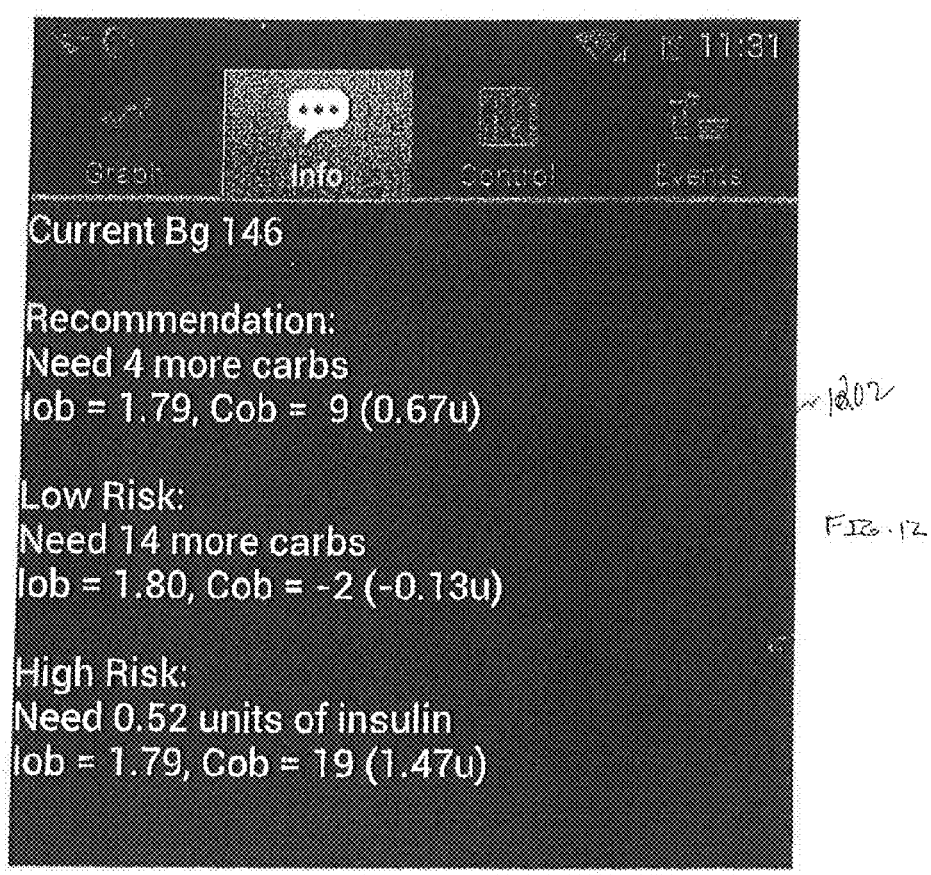
FIG. 12 is a screenshot that may appear on the personal computing device in FIG. 1 and that includes therapeutic recommendations.

FIG. 12 is an exemplary screenshot 1202 that may be appear at the user interface of the personal computing device 104 in FIG. 1.

The illustrated screenshot 1202 identifies the user's current blood glucose level (i.e., 146) and provides three sets of information/recommended actions based, respectively, on the optimal trajectory of the user's blood glucose level (this is labeled "Recommendation"), the upper boundary of the confidence band around the optimal trajectory curve (this is labeled "high risk"), and the lower boundary of the confidence band around the optimal trajectory (this is labeled "low risk").

Each scenario has the relevant stats for its corresponding trajectory—the IOB, COB and implied therapy.

In general, the computer system 100 in FIG. 1 is configured to: calculate a recommended dose of insulin (e.g., a bolus) to deliver or a recommended quantity of carbohydrates to consume based, at least in part, on an amount of carbohydrates that the user has received that is yet to be absorbed by the user (i.e., the carbs-on-board).

In addition, in some implementations, the system can include an occlusion alarm that leverages the techniques disclosed herein. The occlusion alarm may be implemented as part of an overall alarm scheme, as discussed herein.

Figure 13:
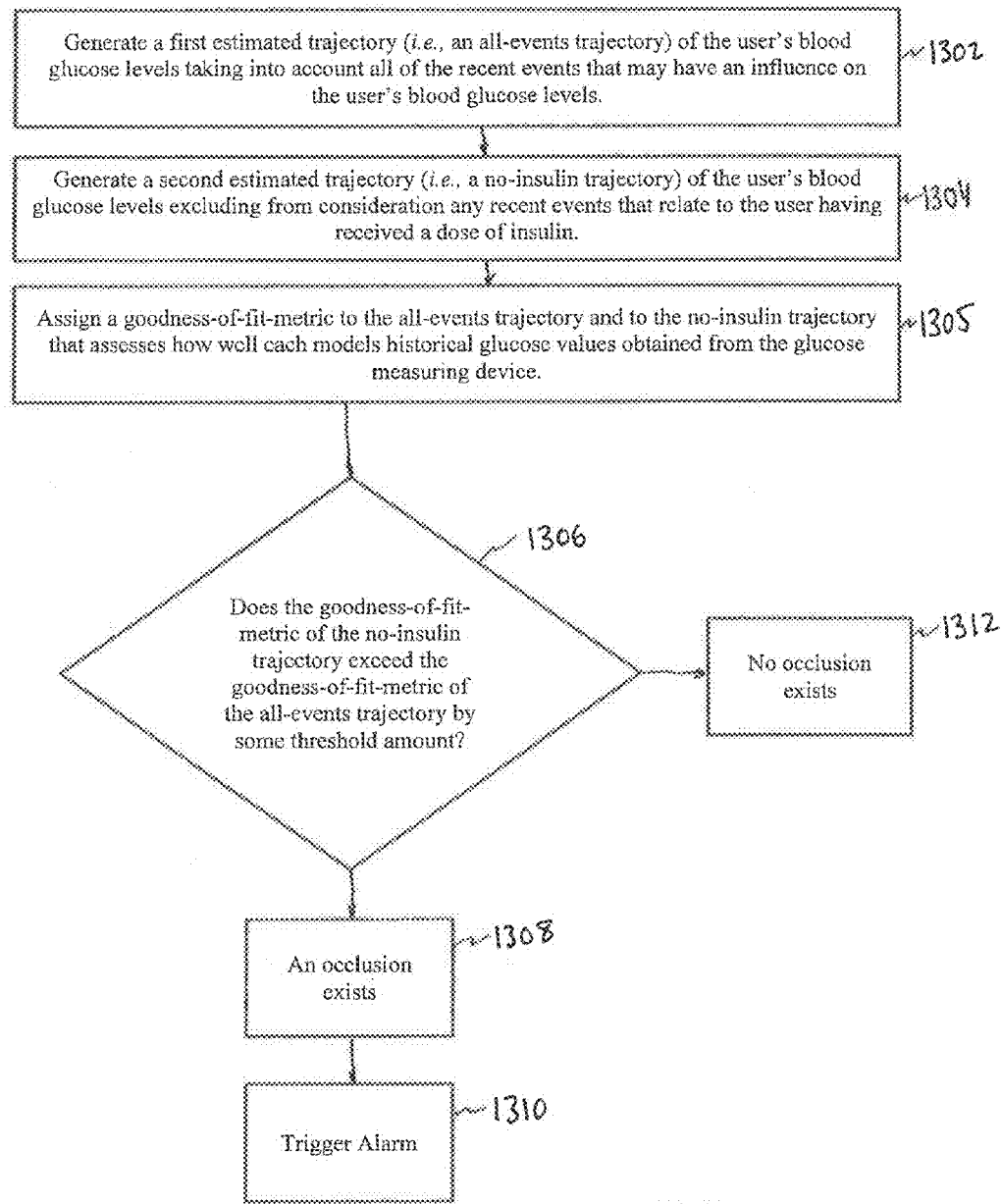
FIG. 13 is a flowchart of a process that can be performed in connection with the system of FIG. 1 for determining whether and alarming if an occlusion exists.

FIG. 13 is a flowchart showing an exemplary process performed by the computer-based processor 108 to detect and alarm if an insulin pump occlusion has occurred.

According to the illustrated process, in order to detect whether the user's insulin pump may have an occlusion (e.g., a blockage that is preventing the delivery of dosed insulin to the user), the system 100 (e.g., the computer-based processor 108) generates (at 1302) a first estimated trajectory (i.e., an all-events trajectory) of the user's blood glucose levels taking into account all of the recent events that may have an influence on the user's blood glucose levels. In some implementations, generating the all-events trajectory is very much like (or identical to) the process discussed above for generating the optimal trajectory of the user's blood glucose levels.

According to the illustrated process, the system 100 (e.g., the computer-based processor 108) also generates (at 1304) a second estimated trajectory (i.e., a no-insulin trajectory) of the user's blood glucose levels. Generating the no-insulin trajectory is similar generating the optimal trajectory of the user's blood glucose levels, discussed above, but it excludes from consideration any recent events that relate to the user receiving a dose of insulin.

Each trajectory is assigned (at 1305) a goodness-of-fit-metric by the system that assesses how well they model the historical glucose values obtained from the glucose measuring device 102. The system 100 then compares (at 1306) the all-events trajectory to the no-insulin trajectory and, if the goodness-of-fit-metric of the no-insulin trajectory exceeds the goodness-of-fit-metric of the all-events trajectory by some threshold value, then the system 100 concludes (at 1308) that an occlusion exists.

In some implementations, and according to the illustrated implementation, the system 100, upon making such a conclusion, triggers an alarm (at 1310). If the system 100 does not make such a conclusion (1312), then no alarm is triggered.

In addition, in some implementations, the system 100 includes high blood glucose alarms that leverage the techniques disclosed herein as well.

Standard alarms such as threshold and short term predictions of future blood glucose levels are easily achieved. However, a patient very often knows that their short term glucose values are likely to be out-of-range and alarm-worthy yet they have already corrective taken action to mitigate the glucose excursion by taking insulin or eating carbohydrates. Thus, simplistic alarms may generate annoying and unnecessary alarms causing so called alarm-fatigue. The time delay of insulin or carbohydrate action in a user can, in some situations, result in there being a meaningful amount of time where the current or near-future blood glucose values are out of range, however, where the future, more steady-state predicted glucose values are in range.

In various implementations, the computer-based processor 108 can facilitate one or more alarms based on a long-term, more steady-state predicted level of blood glucose values—as reflected, for example, in the optimal blood glucose trajectory—rather than on near term or current glucose levels.

In some implementations, the system 100 (more particularly, the personal computing device 104) includes one or more alarms based on a long-term, more steady-state condition (e.g., as represented at a point in the future along the optimal projected blood glucose levels rather than (or in addition to) near term alarms. This can, in some instances, provide the great benefit of taking into account the patient's recent therapy actions (as inputted events) and will only alarm if the system surmises that the future glucose levels nevertheless will be out of a desired range.

This can reduce so-called alarm-fatigue. In addition, because the long-term, more steady state values can be targeted to a much tighter range than absolute, current or near-term glucose values (due to the mitigation of alarm-fatigue), the long term, more steady-state alarms can be much more aggressively tuned and thus provide better degree of therapy control to the patient.

For example, if a patient with a carb ratio of 10 grams/unit eats a fast-acting glucose load of 50 grams that moves her blood glucose level from 120 to 200 over the course of 30 minutes, but concurrently takes the proper amount of offsetting insulin (5 units, fast acting insulin) the system 100 will likely anticipate that the blood glucose values will return to the normal range. In the case of a long term, steady-state alarm, no alarm would sound, whereas a system with a near term or current threshold alarm would likely be set off at 200 (assuming the user has recommended control intentions).

If the glucose continues to rise beyond what would be expected of a 50 gram load (if, for example, the patient underestimated the grams of carbohydrate and it was actually 75 grams) then the future glucose value will rise accordingly and possibly will rise above a steady-state alarm level. Once notified of this, the patient can take an appropriate corrective dose and enter the corrective event into the system. After this is done, the system 100 will not alarm for the steady state alarm unless the system further predicts that the steady state level moves again out of range.

Another possible alarm approach is to create a bolus calculator alarm that will alarm based on the current requirement of insulin or carbohydrates. If the calculator result is a therapy of greater than a certain value, the alarm would go off.

A further use of the techniques disclosed herein would be to combine the steady-state or calculator alarms with a threshold or short term glucose prediction alarm. A typical combination would put a high near term alarm with a high steady state alarm and equivalently a low near term alarm with a low steady state alarm. An alarm of this nature might prevent the steady state alarms from going off when there is no near-term risk and thus eliminates potential false steady-state alarms that the system would later see are not a concern as time progresses.

All alarms may be set off on the personal computing device and/or may be transmitted to one or more remote devices for remote alarming.

A number of embodiments have been described. Nevertheless, it will be understood that various modifications may be made without departing from the spirit and scope of the invention.

The glucose measurement device 102 can be a glucose meter. A glucose meter is a medical device for determining the approximate concentration of glucose in a user's blood. Typically, a small drop of blood, obtained by pricking the skin with a lancet, is placed on a disposable test strip that the meter reads and uses to calculate the blood glucose level. The meter then displays the level, for example, in mg/dl or mmol/l. In various implementations, the glucose meter may be adapted to automatically transmit the level to the personal computing device 104 or a user may read his or her level from the meter's display and then manually enter the blood glucose level into the personal computing device via the computer-based input device.

The personal computing device 104 can be any type of personal computing device. However, preferably, it is compact, easy to carry and able to handle the processing functionality disclosed herein relatively quickly.

The glucose measuring device 102 and the personal computing device 104 can be configured to communicate over a wired connection.

The functionality of the glucose measurement device 102 and/or the personal computing device 104 can be incorporated into different products. For example, the functionality of the personal computing device 104 can be incorporated into an insulin pump.

In some implementations, when the computer-based processor accesses the one or more generic, normalized curves, it actually accesses data representing the curves. A physical representation of the actual generic, normalized curves is not necessary.

The model outputs may also be used to forecast future glucose values by applying equation (1) into the future. Additionally, the historical glucose values may be taken as given or a temporal shift can be applied to the times of the historical glucose values, if there is a known lag between the sensing devices values and real time glucose values and an estimate can be provided by the user as to the time differential between the two.

Additionally, in some implementations, one or more aspects of the functionality provided by the personal computing device 104 may be implemented by a medical device, such as a glucose sensing system or an insulin pump. In general, this streamlines the form-factor for the user.

In general, the input functionality of the personal computing device 104 allows for entry of data regarding events, including insulin doses, carbohydrate intake, exercise and temporary changes to basal insulin (both increased and decreased). These events are stored in the memory area of the computing device and are available to algorithms run by the processor. The interactive display typically allows for adding, removing and changing event data in the stored memory to properly reflect a patient's history.

Some events may be communicated to the computing device directly from a medical device, such as an insulin pump, glucose meter or continuous glucose meter. Insofar as event data is transmitted electronically from another device, that data need not also be entered by the user. Other methods of entering events into the device may be to use accelerometers, heart-rate monitors and/or other electronic sensing devices that may be used to infer data regarding an event of some sort, be it exercise or otherwise.

In general, the input functionality of the personal computing device 104 further allows users to enter static patient specific parameters associated with diabetes management. Such parameters include estimates of one or more of the following: the user's insulin sensitivity, carbohydrate to insulin ratios, basal rate, duration of insulin action, target blood glucose value, a duration of effect associated with exercise done by the user, exercise per hour to carbohydrate ratio (representing the number of carbohydrates needed to offset the blood glucose lowering effect of one hour of exercise), and target glucose range. Each of these parameters may have a single value or a schedule of values that vary by hour of day and/or day of week. In some implementations, it may be feasible to enter values for other parameters not specifically mentioned herein.

The communication protocol can interface directly with an external glucose sensing device that provides regular glucose values. The computing device can poll or asynchronously receive data from the external glucose sensing device and store it in the memory for later algorithmic consumption. The external glucose data may also be shown on the display to provide context of algorithmic outputs.

Changes in basal rates may be modeled as numerous small insulin events, either positive or negative magnitudes for increases and decreases of temporary basal rates, respectively. Exercise events may be modeled as negative carbohydrate events with duration of the length of the activity, or may be modeled more elaborately with a separate exercise 'absorption' curve—that is, a curve describing how the exercise impacts blood glucose. A simple linear curve or constant function is an example of such an alternative exercise absorption curve.

The system described above provides model outputs that result from combining the heretofore mentioned user-entered-patient-specific parameters, the vector of events, the historical glucose trace, a generic, pharmacodynamics, insulin absorption curve, a generic, mixed-meal, carbohydrate absorption curve, and a generic curve for the effects of exercise. The model outputs can be plotted to show future blood glucose visualizations and predictions. In another use of the invention, the system is able to infer insulin and/or carbohydrate therapy recommendations from the model outputs.

The invention creates model outputs by using the above described parameterization of the events in the history. A solution is a set of parameters for each of the events and a single point of reference from which the absorption profiles can be applied. In one embodiment of the system, the current time is the reference point and the parameterized absorption curves for both insulin and carbohydrates describe how the blood glucose varies before and after the reference point. The parameters for each event include the start time of absorption, the magnitude of the event and the duration of the event. These parameters, combined with the normalized insulin and carbohydrate absorption curves, the insulin sensitivity factor and the carbohydrate ratio provide delta changes to the blood glucose from the reference point.

Because there may be exogenous factors that affect blood glucose values such as miss-estimated basal rates, physiological events that are not modeled by the system, or simply events that have been neglected to be entered by the user, a further embodiment of the invention allows for an exogenous drift in the blood glucose values to help forecast short term glucose values. This drift event can be modeled as the insulin and carbohydrate events have been above, with a parameter set of start time, magnitude and duration accompanied by a fixed, normalized drift absorption curve. One possible function that may yield good results in this regard is a Gaussian function. That is, the system allows for constrained glucose variation in the shape of a cumulative Gaussian function to allow for a better model fit. The system can include this drift event in the solution search for the carbohydrate and insulin event parameters or can do it in a separate optimization, holding the known events with a fixed set of parameters found in an initial search. The latter formulation of the algorithm tends to yield better results. There are many other variations one may use to improve the fit around the core parameterization of the insulin and carbohydrate events and this is just one of them.

The terms future blood glucose curve, and the like, are used throughout the specification. It should be understood that these terms refer not only to the curve itself, but also to the underlying data that is represented by the curve.

The computer-based processor can be any type of processor and can include one or more processors physically located close to each or remotely located relative to each other. Similarly, the computer-based memory can be any type of memory device or technology and can include one or more memory devices located physically close to each other or in remote locations relative to each other.

The order of the methods disclosed herein can vary. In addition, in some implementations, certain steps may be omitted and/or certain other steps may be added.

A non-transitory, computer-readable medium can be provided that stores instructions executable by a computer-based processor to perform steps disclosed in connection with the various processes disclosed herein.

Other implementations are within the scope of the claims.

What is claimed is:

1. A method for managing diabetes, the method comprising:
    receiving, from a computer-based user interface, user-specified information about one or more events influential on a blood glucose level of a user, the user-specified information about the one or more events influential on the blood glucose level of the user describing: (a) consumption of carbohydrates by the user, (b) a discrete dose of insulin received by the user, or (c) a quantity of exercise completed by the user;
    receiving, from a continuous glucose monitor, a plurality of blood glucose levels for the user after receiving the user-specified information;
    accessing, in a computer-based memory, one or more normalized curves, each having a shape that represents generically any of: (i) how a dimensionless unit of carbohydrates consumed is fractionally absorbed by a generic user as a function of percent of total carbohydrate absorption time, (ii) how a dimensionless unit of insulin is fractionally absorbed by the generic user as a function of percent of total insulin absorption time, or (iii) how a dimensionless quantity of exercise fractionally takes effect on the generic user as a function of percent of total time for the exercise to take full effect on the user;
    generating a nominal trajectory of the blood glucose level of the user by parameterizing one or more of the generic, normalized curves with the user-specified information about the one or more events influential on the blood glucose level of the user;
    applying an iterative search to generate one or more other trajectories based on the nominal trajectory by adjusting different types of the user-specified information at different rates based on an expected accuracy of the user-specified information until the iterative search converges on one or more of:
        an amount of, time of, and absorption time of one or more of the following:
            (a) carbohydrates actually consumed by the user,
            (b) a discrete dosage of insulin actually received by the user, and
            (c) a quantity of exercise actually completed by the user,
    that produces a trajectory that matches the plurality of blood glucose levels received after the time of the one or more events more closely than the nominal trajectory; and
    delivering insulin to the user based on the trajectory generated by the iterative search.

2. The method of claim 1, wherein delivering insulin to the user comprises determining an insulin on board for the user based on the trajectory generated by the iterative search.

3. The method of claim 1, further comprising triggering an alarm when the trajectory generated by the iterative search indicates that insulin was not actually delivered.

4. The method of claim 1, wherein the user-specified information about the one or more events influential on the blood glucose level of the user includes at least two of: (a) a consumption of carbohydrates by the user, (b) a discrete dose of insulin received by the user, and (c) a quantity of exercise completed by the user.

5. The method of claim 1, further comprising displaying the trajectory generated by the iterative search, the trajectory including future projected blood glucose levels of the user.

6. The method of claim 5, further comprising displaying an upper projection above the trajectory generated by the iterative search and a lower projection below the trajectory generated by the iterative search, the upper projection and the lower projection indicative of a confidence band reflecting a degree of confidence in the future projected blood glucose levels.

7. The method of claim 6, wherein displaying an upper projection above the trajectory generated by the iterative search and a lower projection below the trajectory generated by the iterative search further comprises super-imposing the upper projection and the lower projection over the trajectory generated by the iterative search.

8. The method of claim 1, wherein the iterative search includes a gradient descent algorithm seeded with a midpoint of a constrained range for one or more parameters used to generate the nominal trajectory, the one or more parameters including the user-specified information.

9. The method of claim 1, wherein applying an iterative search to generate one or more other trajectories is continued until stopping conditions are met.

10. The method of claim 1, wherein the user-specified information includes a start time of a given event and a quantity associated with the given event.

11. The method of claim 10, further comprising determining a duration for the given event based on the start time and the quantity associated with the given event, wherein the nominal trajectory is based on the duration for the given event.

12. The method of claim 1, wherein the trajectory generated by the iterative search includes a first portion that overlaps in time with at least one of the plurality of blood glucose levels received from the continuous glucose monitor, and a second portion that extends as future projected blood glucose levels.

13. The method of claim 1, wherein the nominal trajectory is further based on one or more additional factors including: an insulin-to-carbohydrate ratio, an insulin sensitivity factor, and a time of carbohydrate absorption.

14. The method of claim 13, wherein at least one of the one or more additional factors has a value that depends on a time of day.

15. A method for determining when to trigger an occlusion alarm when managing diabetes, the method comprising:
receiving insulin delivery data from an insulin pump, wherein the insulin delivery data relates to one or more doses of insulin believed to have been received by a user;
receiving, from a continuous glucose monitor, a plurality of blood glucose levels for the user after receiving the insulin delivery data;
receiving user-specified information;
accessing, in a computer-based memory, one or more normalized curves, each having a shape that represents generically any of: (i) how a dimensionless unit of carbohydrates consumed is fractionally absorbed by a generic user as a function of percent of total carbohydrate absorption time, (ii) how a dimensionless unit of insulin is fractionally absorbed by the generic user as a function of percent of total insulin absorption time, or (iii) how a dimensionless quantity of exercise fractionally takes effect on the generic user as a function of percent of total time for the exercise to take full effect on the user;
generating a nominal trajectory of the blood glucose levels of the user by parameterizing one or more of the generic, normalized curves with the insulin delivery data and parameterization of the user-specified information;
applying an iterative search to generate one or more other trajectories based on the nominal trajectory by adjusting different types of the user-specified information at different rates based on an expected accuracy of the user-specified information until the iterative search converges on one or more of:
an amount of, time of, and absorption time of one or more of the following:
(a) carbohydrates actually consumed by the user,
(b) a discrete dosage of insulin actually received by the user, and
(c) a quantity of exercise actually completed by the user,
that produces a trajectory that matches the plurality of blood glucose levels received after receiving the insulin delivery data more closely than the nominal trajectory;
generating one or more second estimated trajectories using normalized curves that exclude any insulin deliveries;
comparing a fit of the one or more second estimated trajectories to the trajectory generated by the iterative search using insulin delivery data to determine a likelihood that insulin was not actually delivered; and
triggering a sensory alarm if the likelihood is above a certain threshold.

16. The method of claim 15, wherein generating one or more second estimated trajectories comprises applying the iterative search to generate one or more other trajectories based on the nominal trajectory by adjusting one or more parameterizations of the generic, normalized curves until the iterative search converges on one or more of:
an amount of, time of, or absorption time of one or more of the following:
(a) carbohydrates actually consumed by the user,
(b) a discrete dosage of insulin actually received by the user, or
(c) a quantity of exercise actually completed by the user,
that produces a trajectory that matches the plurality of blood glucose levels received after receiving the insulin delivery data more closely than the nominal trajectory.

17. The method of claim 15, wherein the user-specified information includes a start time of a given event and a quantity associated with the given event.

18. The method of claim 17, further comprising determining a duration for the given event based on the start time and the quantity associated with the given event, wherein the nominal trajectory is based on the duration for the given event.

19. The method of claim 15, wherein the user-specified information includes at least one of: (a) a consumption of carbohydrates by the user, (b) a discrete dose of insulin received by the user, and (c) a quantity of exercise completed by the user.

20. The method of claim 15, further comprising displaying the trajectory generated by the iterative search.

21. The method of claim 20, further comprising displaying an upper projection above the trajectory generated by the iterative search and a lower projection below the trajectory generated by the iterative search, the upper projection and the lower projection indicative of a confidence band reflecting a degree of confidence in future projected blood glucose levels.

22. The method of claim 21, wherein displaying an upper projection above the trajectory generated by the iterative search and a lower projection below the trajectory generated by the iterative search further comprises super-imposing the upper projection and the lower projection over the trajectory generated by the iterative search.

23. The method of claim 15, wherein the trajectory generated by the iterative search includes a first portion that overlaps in time with at least one of the plurality of blood glucose levels received from the continuous glucose monitor, and a second portion that extends as future projected blood glucose levels.

24. The methods of claim 15, wherein the nominal trajectory is further based on one or more additional factors including: an insulin-to-carbohydrate ratio, an insulin sensitivity factor, and a time of carbohydrate absorption.

25. The methods of claim 24, wherein at least one of the one or more additional factors has a value that depends on a time of day.

26. The method of claim 15, wherein the sensory alarm includes an audible alarm or a tactile alarm.

27. The method of claim 15, wherein the iterative search includes a gradient descent algorithm seeded with a midpoint of a constrained range for one or more parameters used to generate the nominal trajectory, wherein the generic, normalized curves are based on the one or more parameters.

28. The method of claim 15, wherein applying an iterative search to generate one or more other trajectories is continued until stopping conditions are met.

29. A system for managing diabetes, the system comprising:
a control device comprising:
a user interface configured to obtain user-specified information about one or more events influential on a blood glucose level of a user;
one or more processors; and
one or more non-transitory storage media storing instructions that, when executed by the one or more processors, are configured to cause the control device to perform operations, the operations comprising:
receiving the user-specified information about the one or more events influential on a blood glucose level of the user describing one or more of: (a) a consumption of carbohydrates by the user, (b) a discrete dose of insulin received by the user, and (c) a quantity of exercise completed by the user
receiving a plurality of blood glucose levels for the user after receiving the user-specified information;
accessing one or more normalized curves, each having a shape that represents generically any of: (i) how a dimensionless unit of carbohydrates consumed is fractionally absorbed by a generic user as a function of percent of total carbohydrate absorption time, (ii) how a dimensionless unit of insulin is fractionally absorbed by the generic user as a function of percent of total insulin absorption time, or (iii) how a dimensionless quantity of exercise fractionally takes effect on the generic user as a function of percent of total time for the exercise to take full effect on the user;
generating a nominal trajectory of the blood glucose levels of the user by parameterizing one or more of the generic, normalized curves with the user-specified information about the one or more events influential on the blood glucose level of the user;
applying an iterative search to generate one or more other trajectories based on the nominal trajectory by adjusting different types of the user-specified information at different rates based on an expected accuracy of the user-specified information until the iterative search converges on one or more of:
an amount of, time of, or absorption time of one or more of the following:
(a) carbohydrates actually consumed by the user,
(b) a discrete dosage of insulin actually received by the user, and
(c) a quantity of exercise actually completed by the user,
that produces a trajectory that matches the plurality of blood glucose levels received after the time of the one or more events more closely than the nominal trajectory; and
generating a command to deliver insulin to the user based on the trajectory generated by the iterative search; and
an insulin pump configured to deliver insulin to the user based on the command to deliver insulin.

30. The system of claim 29, further comprising a continuous glucose monitor configured to communicate the plurality of blood glucose levels of the user to the control device.

31. The system of claim 29, wherein the operations further comprise generating one or more second estimated trajectories that exclude any insulin deliveries by applying the iterative search to generate one or more other trajectories based on the nominal trajectory by adjusting one or more parameterizations of the generic, normalized curves until the iterative search converges on one or more:
an amount of, time of, or absorption time of one or more of the following:
(a) carbohydrates actually consumed by the user,
(b) a discrete dosage of insulin actually received by the user, and
(c) a quantity of exercise actually completed by the user, that produces a trajectory that matches the plurality of blood glucose levels received after the time of the one or more events more closely than the nominal trajectory.

32. The system of claim 31, further comprising an alarm generation device configured to generate an alarm based on an alarm message from the control device, wherein the operations further comprise:
comparing a fit of the one or more second estimated trajectories to the trajectory generated by the iterative search using insulin delivery data to determine a likelihood that insulin was not actually delivered; and
generating the alarm message if the likelihood is above a particular threshold.

33. The system of claim 29, further comprising a display configured to display the trajectory generated by the iterative search, the trajectory including future projected blood glucose levels of the user.

34. The system of claim 33, wherein the display is further configured to display an upper projection above the trajectory generated by the iterative search and a lower projection below the trajectory generated by the iterative search, the upper projection and the lower projection indicative of a confidence band reflecting a degree of confidence in the future projected blood glucose levels.

35. The system of claim 34, wherein the display is further configured to super-impose the upper projection and the lower projection over the trajectory generated by the iterative search.

36. A system comprising:
an insulin pump configured to deliver insulin to a user;
a control device comprising:
one or more processors; and
one or more non-transitory storage media storing instructions that, when executed by the one or more processors, are configured to cause the control device to perform operations, the operations comprising:

receiving insulin delivery data from the insulin pump, wherein the insulin delivery data relates to one or more doses of insulin believed to have been received by the user receiving a plurality of blood glucose levels for the user after receiving the insulin delivery data;

receiving user-specified information accessing one or more normalized curves, each having a shape that represents generically any of: (i) how a dimensionless unit of carbohydrates consumed is fractionally absorbed by a generic user as a function of percent of total carbohydrate absorption time, (ii) how a dimensionless unit of insulin is fractionally absorbed by the generic user as a function of percent of total insulin absorption time, or (iii) how a dimensionless quantity of exercise fractionally takes effect on the generic user as a function of percent of total time for the exercise to take full effect on the user;

generating a nominal trajectory of the blood glucose level of the user by parameterizing one or more of the generic, normalized curves with the insulin delivery data and parameterization of the user-specified information;

applying an iterative search to generate one or more other trajectories based on the nominal trajectory by adjusting different types of the user-specified information at different rates based on an expected accuracy of the user-specified information until the iterative search converges on one or more of an amount of, time of, or absorption time of one or more of the following:
  (a) carbohydrates actually consumed by the user,
  (b) a discrete dosage of insulin actually received by the user, and
  (c) a quantity of exercise actually completed by the user, that produces a trajectory that matches the plurality of blood glucose levels received after receiving the insulin delivery data more closely than the nominal trajectory;

generating one or more second estimated trajectories using normalized curves that exclude any insulin deliveries;

comparing a fit of the one or more second estimated trajectories to the trajectory generated by the iterative search using insulin delivery data to determine a likelihood that insulin was not actually delivered; and generating an alarm command if the likelihood is above a certain threshold; and an alarm generation device configured to generate a sensory alarm based on the alarm command from the control device.

37. The system of claim 36, wherein generating one or more second estimated trajectories comprises applying the iterative search to generate one or more other trajectories based on the nominal trajectory by adjusting one or more parameterizations of the generic, normalized curves until the iterative search converges on one or more of:

an amount of, time of, or absorption time of one or more of the following:
  (a) carbohydrates actually consumed by the user,
  (b) a discrete dosage of insulin actually received by the user, and
  (c) a quantity of exercise actually completed by the user, that produces a trajectory that matches the plurality of blood glucose levels received after receiving the insulin delivery data more closely than the nominal trajectory.

38. The system of claim 36, wherein the control device further comprises a user interface configured to receive the user-specified information, wherein the nominal trajectory is further generated by parameterization of the user-specified information.

39. The system of claim 36, further comprising a display configured to display the trajectory generated by the iterative search, the trajectory including future projected blood glucose levels of the user.

40. The system of claim 39, wherein the display is further configured to display an upper projection above the trajectory generated by the iterative search and a lower projection below the trajectory generated by the iterative search, the upper projection and the lower projection indicative of a confidence band reflecting a degree of confidence in the future projected blood glucose levels.

41. The system of claim 40, wherein the display is further configured to super-impose the upper projection and the lower projection over the trajectory generated by the iterative search.

42. The system of claim 39, wherein the display is further configured to super-impose the one or more second estimated trajectories over the trajectory generated by the iterative search.

43. The system of claim 36, wherein the alarm generation device includes a speaker, a vibrator, or both.

\* \* \* \* \*